(12) United States Patent
Aram et al.

(10) Patent No.: US 7,846,165 B2
(45) Date of Patent: Dec. 7, 2010

(54) METHOD AND APPARATUS FOR ARTHROSCOPIC BONE PREPARATION

(75) Inventors: Luke Aram, Warsaw, IN (US); Dan Auger, Fort Wayne, IN (US); Adam Hayden, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 1096 days.

(21) Appl. No.: 10/812,216

(22) Filed: Mar. 29, 2004

(65) Prior Publication Data

US 2005/0216023 A1 Sep. 29, 2005

(51) Int. Cl.
*A61F 5/00* (2006.01)
(52) U.S. Cl. ...................... 606/86 R; 606/79
(58) Field of Classification Search ............... 606/79, 606/80, 82, 86–89, 96, 103; 125/121
See application file for complete search history.

(56) References Cited

U.S. PATENT DOCUMENTS

| | | | | |
|---|---|---|---|---|
| 4,421,112 A | * | 12/1983 | Mains et al. | 606/88 |
| 4,759,350 A | * | 7/1988 | Dunn et al. | 606/82 |
| 5,060,628 A | * | 10/1991 | Ishida | 125/21 |
| 5,077,902 A | * | 1/1992 | Hitt | 30/394 |
| 5,246,444 A | | 9/1993 | Schreiber et al. | |
| 5,505,738 A | * | 4/1996 | Hempel et al. | 606/82 |
| 5,817,097 A | | 10/1998 | Howard et al. | |
| 5,851,209 A | * | 12/1998 | Kummer et al. | 606/103 |
| 5,911,724 A | * | 6/1999 | Wehrli | 606/88 |
| 2004/0143280 A1 | * | 7/2004 | Suddaby | 606/167 |
| 2005/0070909 A1 | * | 3/2005 | Egger et al. | 606/87 |
| 2006/0030854 A1 | * | 2/2006 | Haines | 606/88 |

* cited by examiner

*Primary Examiner*—Thomas C Barrett
*Assistant Examiner*—Michael J Araj
(74) *Attorney, Agent, or Firm*—Maginot, Moore & Beck

(57) ABSTRACT

A guide system for resecting a bone through incisions of the type utilized for arthroscopic procedures is provided. The guide system comprises a first alignment pin, a second alignment pin and a wire saw. The first alignment pin is configured to be inserted through a first incision into a bone in a first orientation. The second alignment pin is configured to inserted through a second incision into the bone in a second orientation. The first alignment pin and the second alignment pin are configured and oriented to define a resection plane of reference through which the bone is to be resected and the wire saw is configured to be inserted through the first and second incisions to be guided by the first and second alignment pins while being moved to resect the bone.

20 Claims, 18 Drawing Sheets

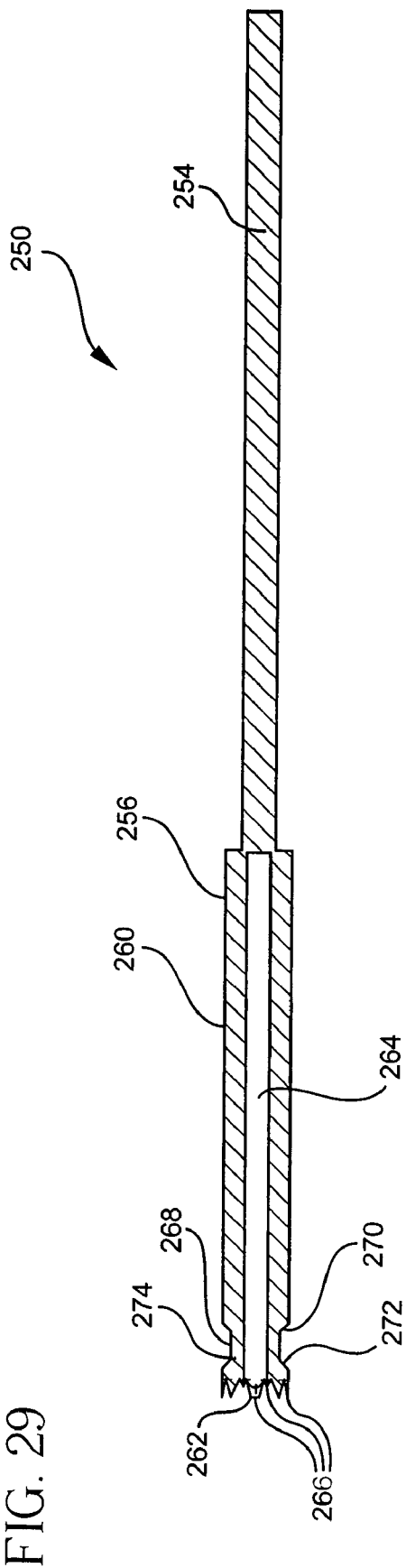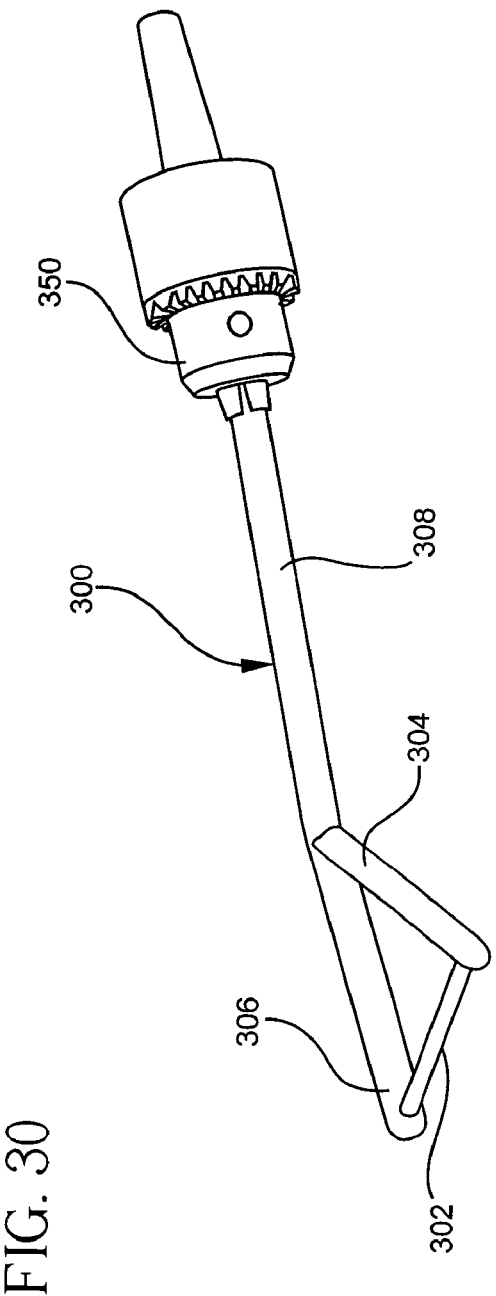
FIG. 29
FIG. 30

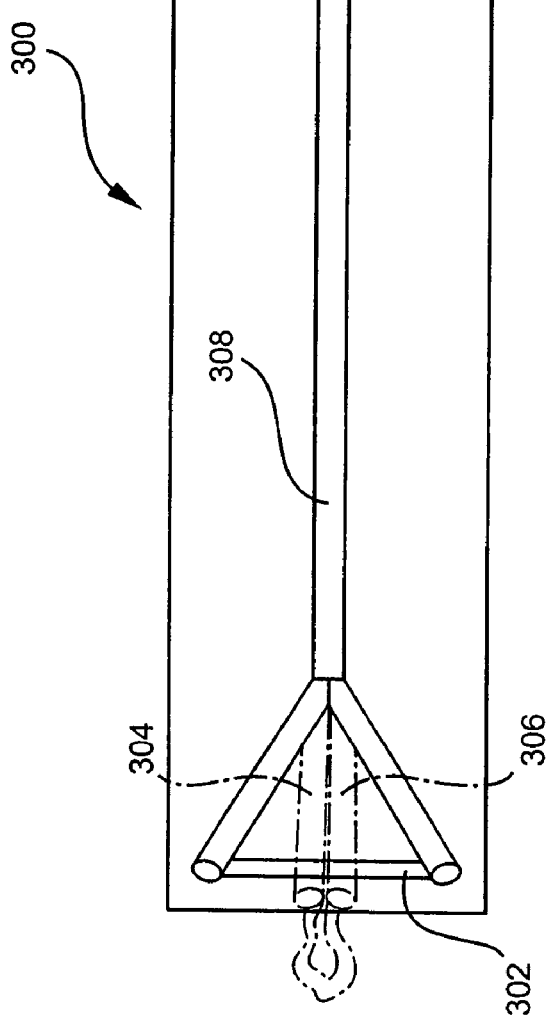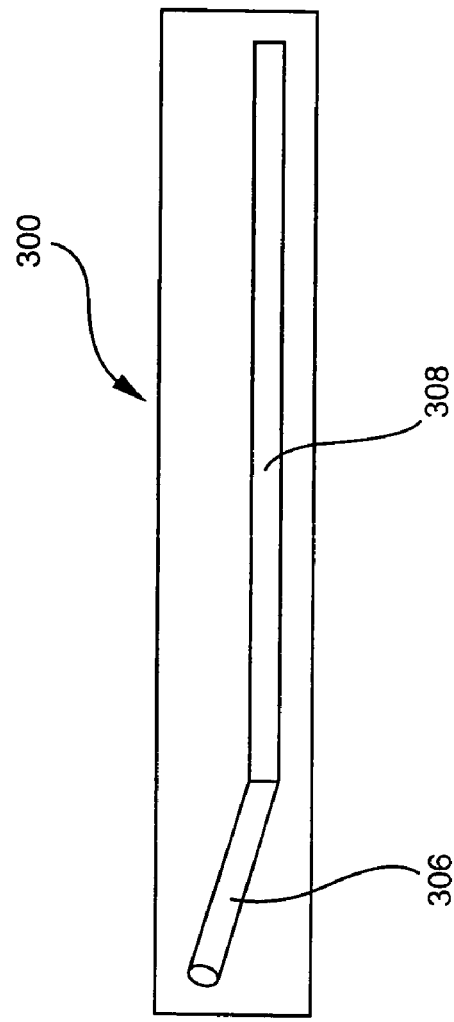
FIG. 31
FIG. 32

METHOD AND APPARATUS FOR ARTHROSCOPIC BONE PREPARATION

BACKGROUND AND SUMMARY

This invention relates generally to methods and apparatus for resecting bones and more particularly to methods and apparatus for resecting bones through a minimally invasive incision.

Current trends in joint replacement surgery suggest that smaller incision size can lead to faster recovery, improved quadriceps function and increased patient satisfaction. Joint replacement surgery typically requires bone resection in preparation for an implant. Traditional instrumentation for orthopaedic implants is designed around an oscillating saw blade used to resect the bone. Cutting blocks, pins and alignment towers place and hold the saw blade in the proper orientation. However, these blocks are large and require a large incision.

When a patient undergoes total knee replacement (TKR) it is common for the patient to stay in the hospital for one to two weeks. Rehabilitation therapy lasts months and most patients do not fully recover for years. Some patients never fully recover. This recovery process poses a substantial psychological and financial strain on TKR patients. Many patients are in the latter years of their lives and this recovery period represents a significant portion of the remaining years.

Many orthopaedic companies offer a "minimally invasive" knee replacement. The claim "minimally invasive," as used with regard to knee replacements, usually refers to an incision of six to ten cm. This is a great improvement over the twenty to thirty cm incision of the past. Peer reviewed articles have already demonstrated the faster recovery, shorter hospital stays, and improved patient satisfaction resulting form using minimally invasive knee replacements. The logical progression would be to decrease the incision size even further. However, the common constraint is a saw blade, the block required to capture that blade and the pins required to secure the block.

The disclosed method uses a saw guided along holes formed in the bone to prepare a bone to receive an implant. Thus, rather than requiring an incision sized to permit insertion of a rotating or reciprocating saw blade, tower and block, the disclosed method requires small incisions to facilitate forming holes, into which pins may be inserted, and guiding a wire saw along the hole or the pins.

One aspect of the disclosure aligns two pins inside the bone to be resected such that those pins describe a surface. A wire cutting saw is then tensed between the pins to resect bone along that surface. This bone cutting method may be accomplished through a true arthroscopic incision (<1 cm).

Thus, the disclosed device and method enables TKR without a large skin incision. Also the method enables the preservation of musculature, ligaments, tendons, nerves and the blood supply. By allowing the surgeon to prepare the bone arthroscopically, the method facilitates reduced tourniquet time, reduced anesthetic requirements, and a reduction in the risk of infection.

According to one aspect of the disclosure a guide system for resecting a bone through incisions of the type utilized for arthroscopic procedures is provided. The guide system comprises a first alignment pin, a second alignment pin and a wire saw. The first alignment pin is configured to be inserted through one of the incisions into a bone in a first orientation. The second alignment pin is configured to be inserted through one of the incisions into the bone in a second orientation. The first alignment pin and the second alignment pin are configured and oriented to define a resection surface of reference through which the bone is to be resected and the wire saw is configured to be inserted through at least one of the incisions to be guided by the first and second alignment pins while being moved to resect the bone.

According to another aspect of the disclosure, the apparatus may further comprise a guide block formed to include a first guide hole extending through the block. The first guide hole is sized to receive a drill sized to form a hole in the bone sized to receive the first alignment pin. The first alignment pin has a length sufficient that the first alignment pin extends completely through the bone with one tip extending beyond the bone on a first side and the second tip extending beyond the bone on the opposite side and into the first guide hole when the guide block is positioned on the opposite side of the bone. The guide block may be formed to include a first saw guide and a second saw guide to guide the saw along the resection plane of reference when the saw is received in the saw guides.

According to yet another aspect of the disclosure the guide pin and wire saw apparatus may also include a saw driver configured to be guided by the first pin through the bone and to drive the saw guided by the saw driver and the second alignment pin through the bone.

According to yet another aspect of the disclosure, the guide pin and wire saw apparatus may also include a saw frame having a shaft adapted to be coupled to an oscillator, a finger coupled to the shaft at one end for movement between a retracted position wherein a second end of the finger is adjacent the shaft and an extended position wherein the second end is displaced from the shaft. The wire saw is coupled to the shaft and the finger adjacent the second end to be tensioned between the shaft and the second finger when the second finger is in the extended position.

According to yet another aspect of the disclosure, a method of resecting a bone of a patient comprises an incising step, a forming step an inserting step and a resecting step. The incising step includes incising the skin and underlying tissue at a first point overlying the bone with an incision having a length less than six centimeters. The forming step includes forming a hole through the bone with an instrument inserted through the incision. The inserting step includes inserting a saw through the incision. The resecting step includes resecting the bone along the formed hole with the inserted saw.

According to still another aspect of the disclosure, an apparatus for resecting a bone comprises a wire saw and a saw driver. The saw driver includes a shaft adapted to be driven by a rotary drill to rotate about an axis. The saw driver also includes a body coupled at a first end to the shaft to be rotated thereby about the axis. The body includes a second end formed to include teeth adapted to cut through the bone and a wall extending between the first end and the second end. The wall is formed to include a driver surface for engaging the wire saw and driving the same during rotation of the body.

Additional features and advantages of the present invention will become apparent to those skilled in the art upon consideration of the following detailed description of preferred embodiments exemplifying the best mode of carrying out the invention as presently perceived.

BRIEF DESCRIPTION OF THE DRAWINGS

The illustrative devices will be described hereinafter with reference to the attached drawings which are given as non-limiting examples only, in which:

FIG. 29 is a sectional view of the adapter tool taken along line 29-29 of FIG. 27;

FIG. 30 is a perspective view of a wire saw secured in a wire saw holder with retractable fingers and the chuck of an oscillatory power tool for oscillating the wire saw in the holder;

FIG. 31 is a plan view of a wire saw and wire saw holder with retractable fingers made from a shape memory alloy showing the saw in a retracted position in phantom lines;

FIG. 32 is an elevation view of the wire saw and wire saw holder of FIG. 31;

Corresponding reference characters indicate corresponding parts throughout the several views. Like reference characters tend to indicate like parts throughout the several views.

DETAILED DESCRIPTION

Figure 1:
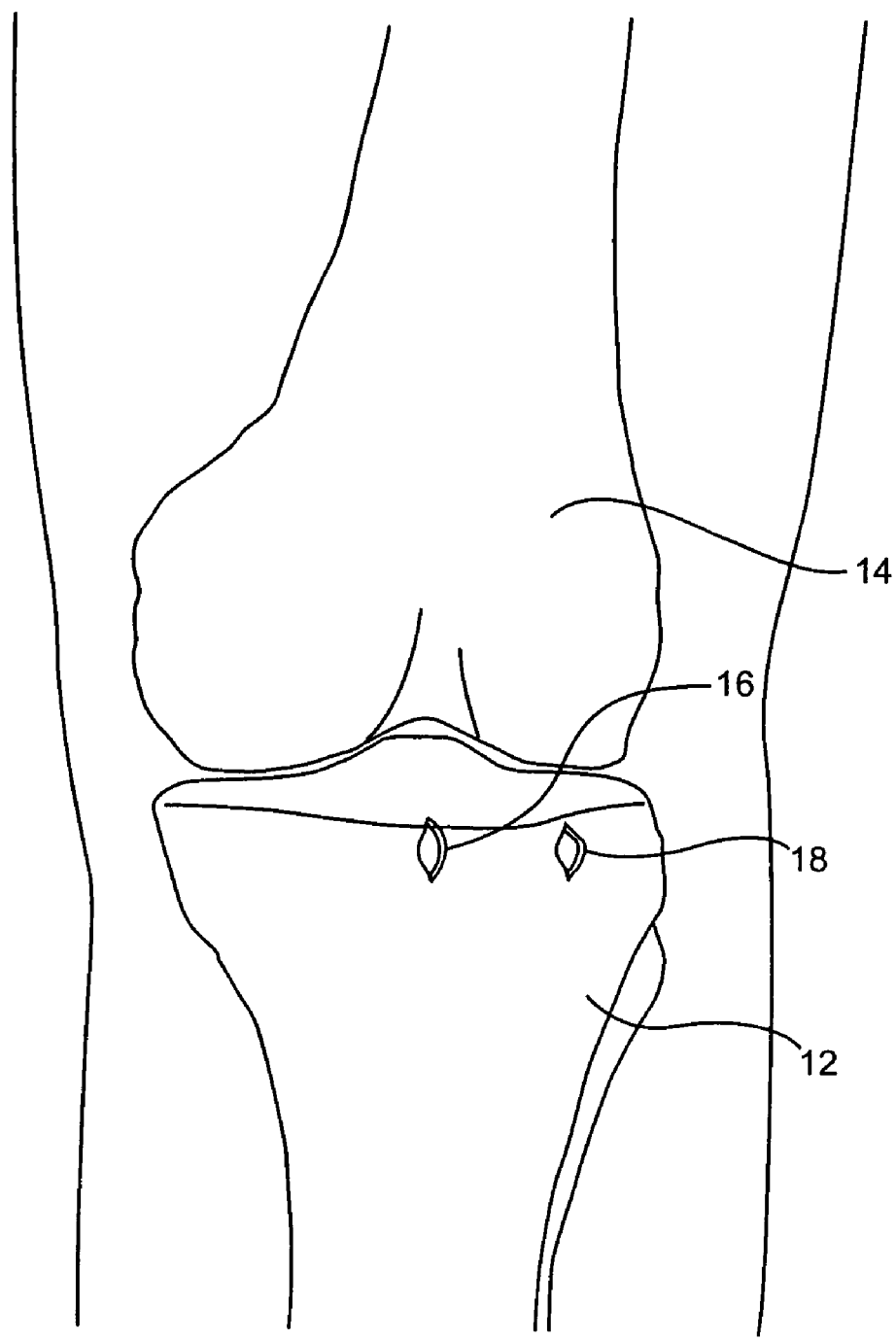
FIG. 1 is a perspective view of a leg of a patient showing the femur and tibia and a portion of the fibula in phantom lines with two arthroscopic incisions through the skin and underlying tissue to expose portions of the tibia in preparation for resection of the tibia.
Figure 2:
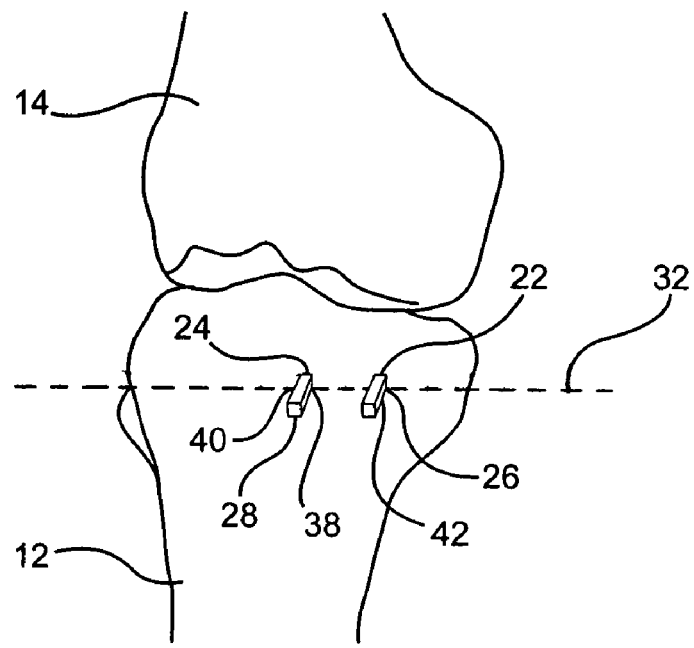
FIG. 2 is a perspective view of the leg of a patient similar to FIG. 1 with the skin and tissue surrounding the bone removed for clarity showing the anterior view of the femur and tibia and also showing two pins inserted into holes extending through the tibia to define a plane of resection.
Figure 3:
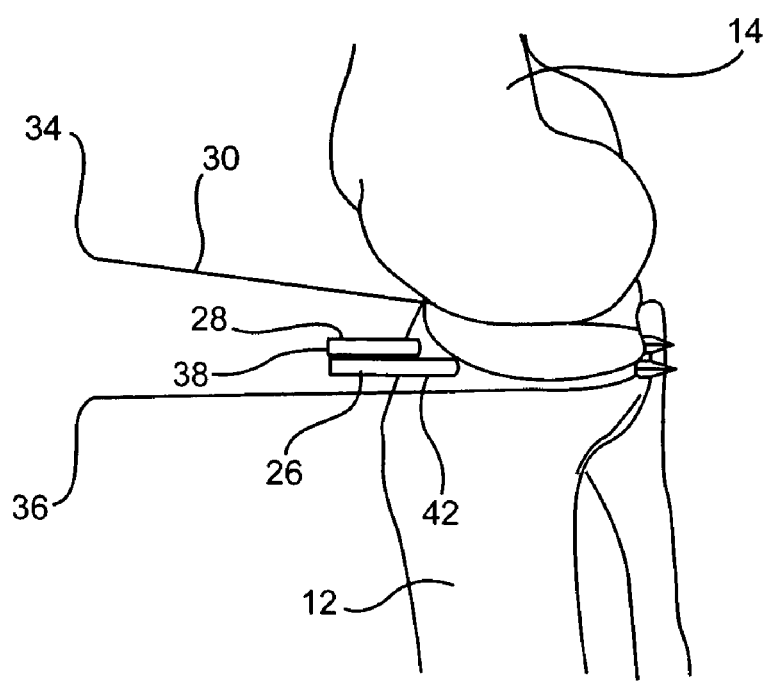
FIG. 3 is a perspective view of the leg of a patient similar to FIG. 2 showing the medial side of the femur, tibia and fibula and also showing the two pins of FIG. 2 extending through the tibia to define a plane of resection and a wire saw extending around the tibia to engage the distal side of the posterior ends of the pins.
Figure 4:
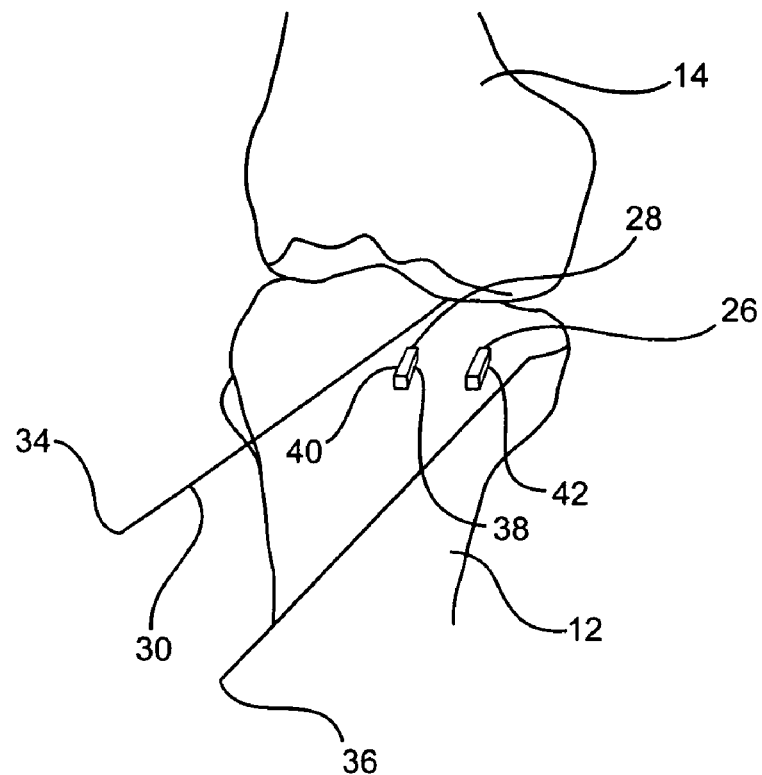
FIG. 4 is a perspective view of the anterior of the femur and tibia similar to FIG. 2 showing the wire saw after it has partially resected the medial portion of the proximal end of the tibia.
Figure 5:
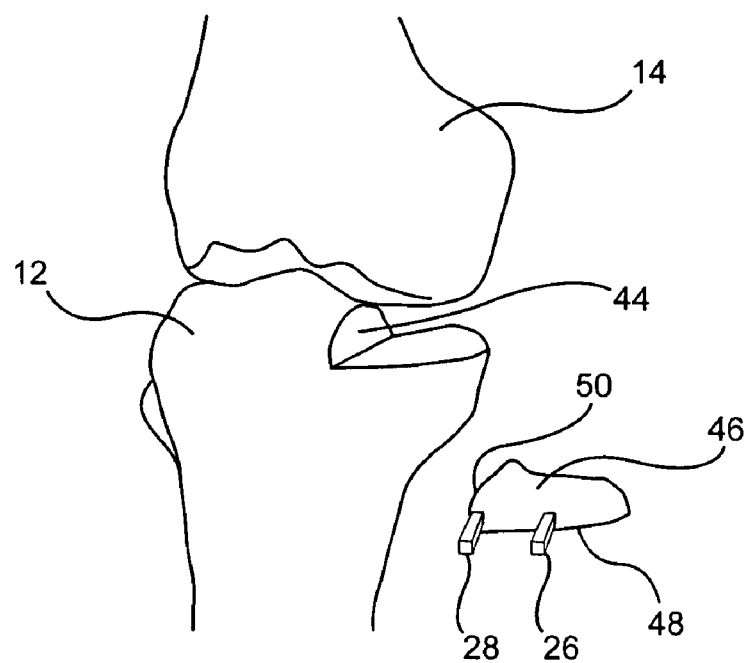
FIG. 5 is a perspective view of the femur and tibia showing the medial portion of the proximal end of the tibia resected leaving a bone chip with the two pins disposed therein.
Figure 6:
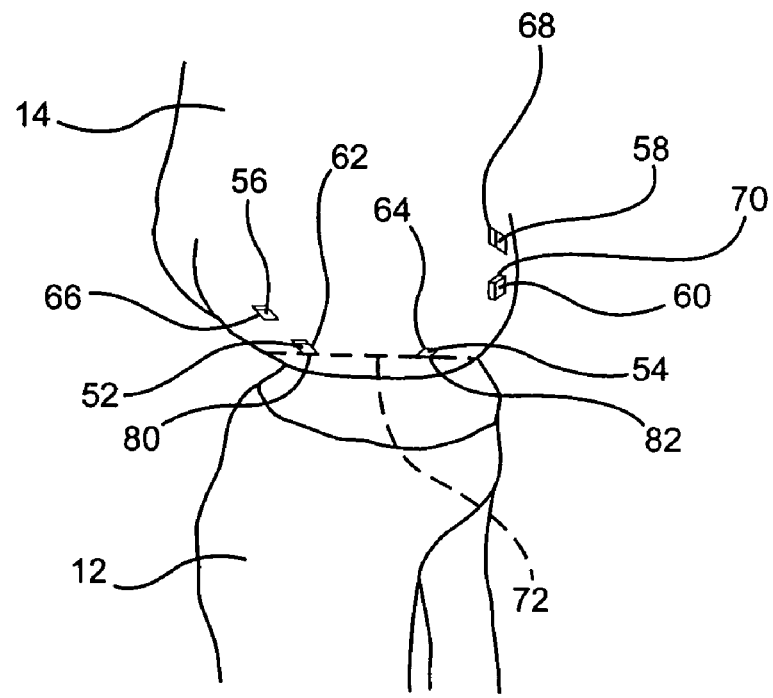
FIG. 6 is a perspective view of the leg of a patient with the skin and tissue surrounding the bone removed for clarity showing the medial side of the femur, fibula and tibia and also showing five pins inserted into holes extending laterally through the femur to define four planes of resection along which a wire saw is to be guided to resect the femur in preparation for a prosthesis.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

As shown for example, in FIGS. 1-5, the tibia 12 of a patient is prepared arthroscopically through small incisions 16, 18 for a knee replacement surgery. The procedure illustrated in FIGS. 1-5 is specific to a uni-condylar implant. However, the steps of the procedure are susceptible for use in a total knee arthroplasty as well. While illustrated with regard to a knee replacement, the teachings of the method and the devices shown are similarly applicable to other joint replacement surgeries such as elbow, ankle, spine, shoulder and hip arthroplasties.

The disclosed devices and methods facilitate arthroscopic preparation of a bone for receipt of a prosthesis. The disclosed devices and methods are also applicable to other procedures in which a bone is required to be cut. Thus, in carrying out the disclosed methods and in utilizing the disclosed devices, arthroscopic incisions 16, 18 are made through the skin and underlying tissue to provide access to an underlying bone through the arthroscopic incisions 16, 18. The disclosed devices and methods facilitate resecting a bone through an incision 16, 18 smaller than the six centimeter incision typically utilized in "minimally invasive" bone resection procedures. The disclosed devices and methods can be used and implemented through incisions 16, 18 of about five, four, three, two and, preferably, one centimeter, or incisions about those sizes. While incisions 16, 18 are only shown with regard to resecting the tibia 12, it is to be understood that, while not specifically illustrated, similar sized incisions may be used to prepare any bone utilizing the disclosed devices and methods.

As shown, for example, in FIGS. 1-5, two pin holes 22, 24 are formed through the tibia 12 in preparation for resecting the tibia 12. The pin holes 22, 24 are formed in an arthroscopic manner or minimally invasive manner utilizing a drill or other boring tool inserted through the incisions 16, 18. It is within the scope of the disclosure to utilize other instruments, including, but not limited to, pins 26, 28 to form holes 22, 24. Any two corresponding locations in the pin holes 22, 24 define a plane through which the tibia 12 is to be resected. Illustratively, since pins 26, 28 are to be inserted in the pin holes 22, 24 to act as a guide against which a wire saw 30 is drawn through the tibia 12, the bottoms of pin holes 22, 24 define a resection plane. As shown, for example in FIGS. 2-4, the metal pins 26, 28 are inserted through incisions 16, 18 and the two holes 22, 24 to provide a metallic resection plane of reference 32 in the tibia 12. Those skilled in the art will recognize that curved holes and pins cam be utilized to form a resection surface of reference and a metallic surface of reference within the scope of the disclosure.

The wire cutting saw 30 is inserted arthroscopically through the incisions 16, 18 to extend to the anterior side of the knee and tensioned against the two pins 26, 28. The ends 34, 36 of the wire saw 30 extend through the arthroscopic incisions 16, 18 used to form the pin holes 22, 24 and insert the pins 26, 28. The wire saw 30 is then reciprocated while pulling upwardly on the wire saw 30 so that resection of the tibia 12 is guided along the distal side 38 and lateral side 40 of the lateral pin 28 and along the distal side 42 of the medial pin 26. Thus the tibia 12 is cut along a surface of reference, illustratively a plane 32, defined by the distal surface 38 of the lateral pin 28 and distal surface 42 of the medial pin 26 from the lateral side 40 of the lateral pin 28 through the medial side of the tibia 12. The tibia 12 is also resected in a plane 44 transverse to the plane 32 of the pins 26, 28 along the lateral side 40 of the lateral pin 28 through the proximal end of the tibia 12. Thus a chip 46 of the medial proximal end of the tibia 12 is removed having a planar bottom surface 48 and a planar lateral surface 50. A shown for example, in FIG. 5, the lateral pin 28 and the medial pin 26 remain disposed in the chip 46 after the tibia 12 is resected.

It is within the scope of the disclosure for the pins 26, 28 to be positioned farther apart if the entire proximal end of the tibia 12 is to be removed. By applying the appropriate tension to the wire saw 30 during reciprocation, the entire proximal end of the tibia 12 may be removed. The resected end may be removed along a single surface defined by the distal surfaces of the pins 26, 28, along two surfaces, one defined by the distal surfaces of the pins 26, 28 and the other transverse thereto or along three surfaces, one defined by the distal surfaces of the pins 26, 28 and the other two transverse thereto. Those skilled in the art will recognize that although shown as being drawn along the distal surfaces of the pins 26, 28, that wire saw 30 could also be drawn along the proximal surfaces of the pins to define a surface of resection.

It is also within the scope of the disclosure for the wire saw 30 to be threaded through one or both of the lateral hole 24 and the medial hole 22 without a pin 26, 28 being inserted through the hole. In such a situation, a portion of the pin hole 22, 24 will be left in the resected bone.

As shown, for example, in FIGS. 6-9, the method of resecting a bone can be used to resect the distal end of the femur 14 arthroscopically in preparation for knee replacement. In preparing the distal end of the femur 14, five arthroscopic incisions are made through the skin and tissue overlying the femur 14. A drill, boring tool or other instrument is inserted into each of the five incisions to form five pin holes 52, 54, 56, 58, 60. Pins 62, 64, 66, 68, 70 are inserted through the incisions and into the five pin holes 52, 54, 56, 58, 60 to define a plurality of metallic resection planes of reference 72, 74, 76, 78.

In the illustrated embodiment, a pin 62, 64, 66, 68, 70 having a parallelogram cross-section is inserted into each pin hole 52, 54, 56, 58, 60. Prior to insertion of the pin 62, 64, 66, 68, 70 into the pin hole 52, 54, 56, 58, 60, an additional reaming step may be performed on one or more pin holes 52, 54, 56, 58, 60 to have the hole 52, 54, 56, 58, 60 assume a cross-section configuration conforming more closely to the cross-section of the pin 62, 64, 66, 68, 70 to be inserted therein. In the illustrated embodiment, pins 62, 64, 66, 68, 70 having a parallelogram cross-section are inserted into the pin holes 52, 54, 56, 58, 60 to provide the finished femur 14 with sharp corners. Thus the additional reaming step would bring the cross-section of the pin holes 52, 54, 56, 58, 60 closer to the parallelogram cross section of the pins 62, 64, 66, 68, 70. It is also within the scope of the disclosure to use pins having a round, square or triangular cross-section. The usage of round pins could eliminate the additional reaming step and reduce the risk of bone fracture resulting from inserting parallelogram pins into round drill holes. Additionally, round pins are typically cheaper to produce.

In describing the procedure of resecting the distal end of the femur 14, the five pins 62, 64, 66, 68, 70 will be referred to respectively as the distal anterior pin 62, the distal posterior pin 64, the proximal anterior pin 66, the proximal posterior pin 68 and the intermediate posterior pin 70.

In the illustrated embodiment, the wire saw 30 (not shown) is first inserted through the incisions made to form the distal anterior pin hole 52 and distal posterior pin hole 54 and through which the distal anterior pin 62 and distal posterior pin 64 were inserted into the femur 14. The wire saw 30 is tensioned against the distal side 80 of the distal anterior pin 62 and the distal side 82 of the distal posterior pin 64 to resect the distal end of the femur 14 along the metallic resection plane of reference 72 (FIG. 6) defined by the distal walls 80, 82 of the distal anterior pin 62 and the distal posterior pin 64, respectively. Following the resection of the distal end of the femur 14, the distal anterior pin 62 and the distal posterior pin 64 remain in the femur 14 to assist with chamfer cuts to follow.

Figure 7:
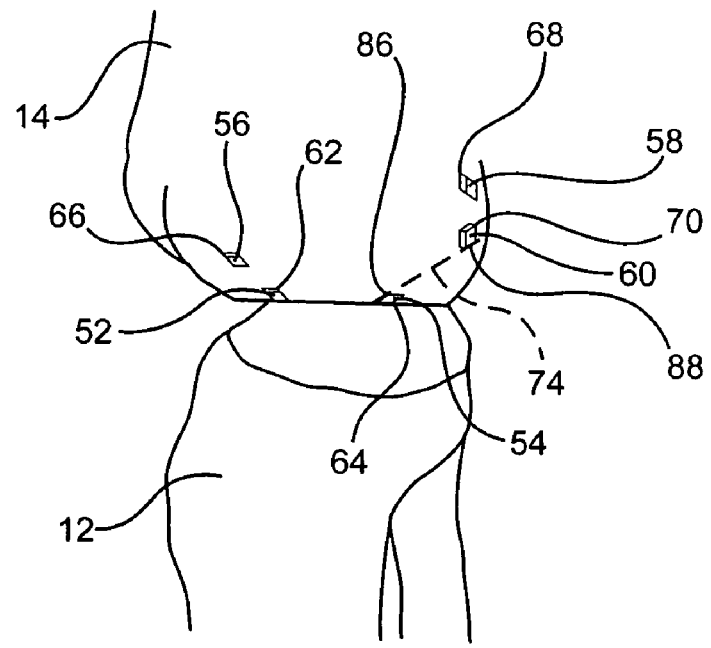
FIG. 7 is a perspective view similar to FIG. 6 after a distal resection has been performed by a wire saw guided against the plane of resection defined by the distal sides of the distal anterior and distal posterior pins and showing a line indicating the plane of resection for a posterior chamfer cut defined by the anterior side of the distal posterior pin and the distal side of the intermediate posterior pin.
Figure 8:
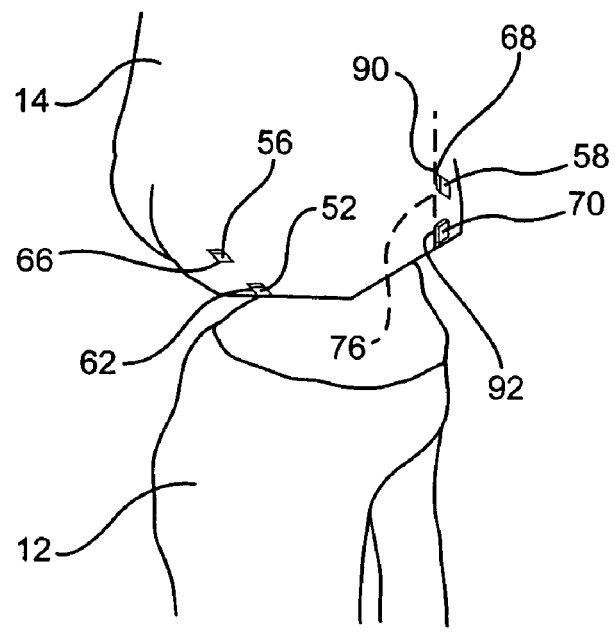
FIG. 8 is a perspective view similar to FIG. 7 after the posterior chamfer cut has been performed with a wire saw and showing a line indicating the plane of resection for a posterior cut defined by the anterior sides of the intermediate posterior pin and the proximal posterior pin.
Figure 9:
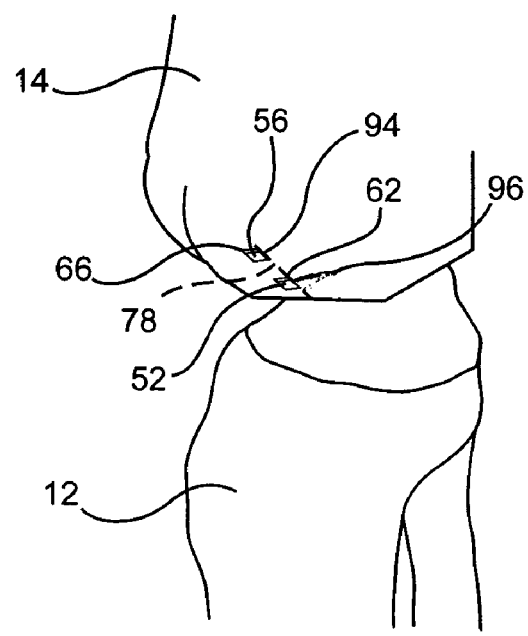
FIG. 9 is a perspective view similar to FIG. 8 after the posterior cut has been performed with a wire saw and showing a line indicating the plane of resection for an anterior chamfer cut defined by the posterior side of the distal anterior pin and the posterior side of the proximal anterior pin.
Figure 10:
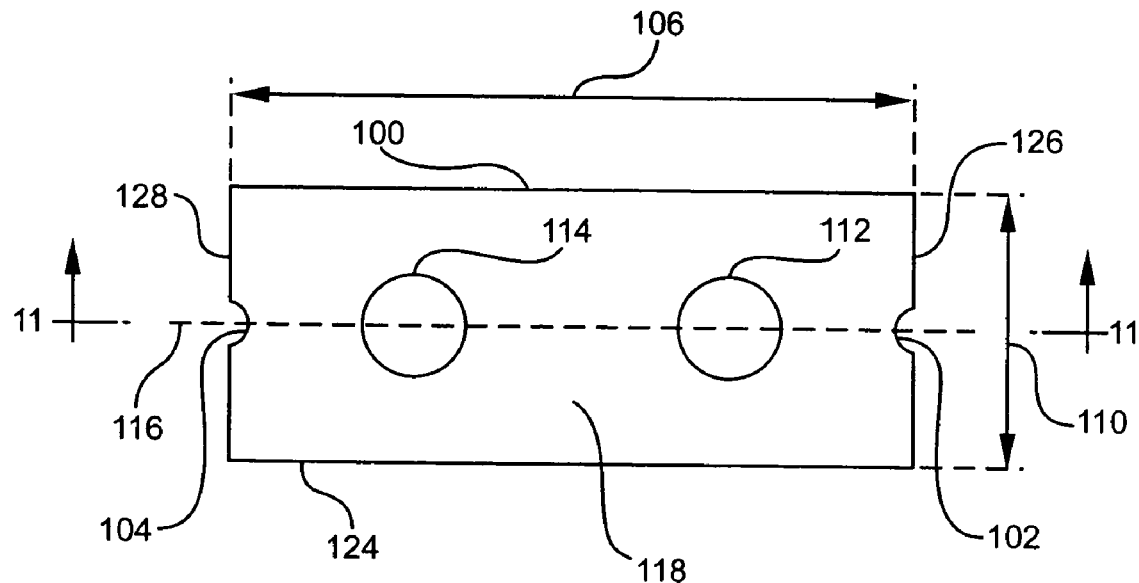
FIG. 10 is a plan view of a tibia preparation guide block including two guide holes for guiding the drilling of pin hole and insertion of pins and two guide slots for guiding reciprocation of the wire saw during resection of the tibia in preparation for a prosthesis.
Figure 11:
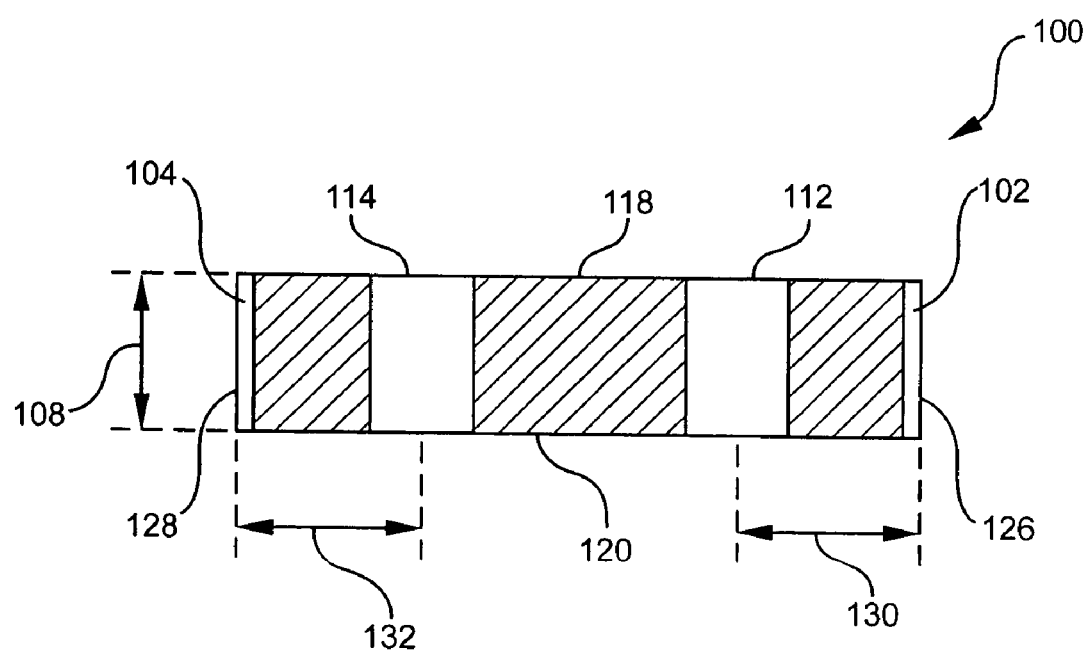
FIG. 11 is a sectional view of the tibia preparation guide block taken along line 11-11 of FIG. 10.
Figure 12:
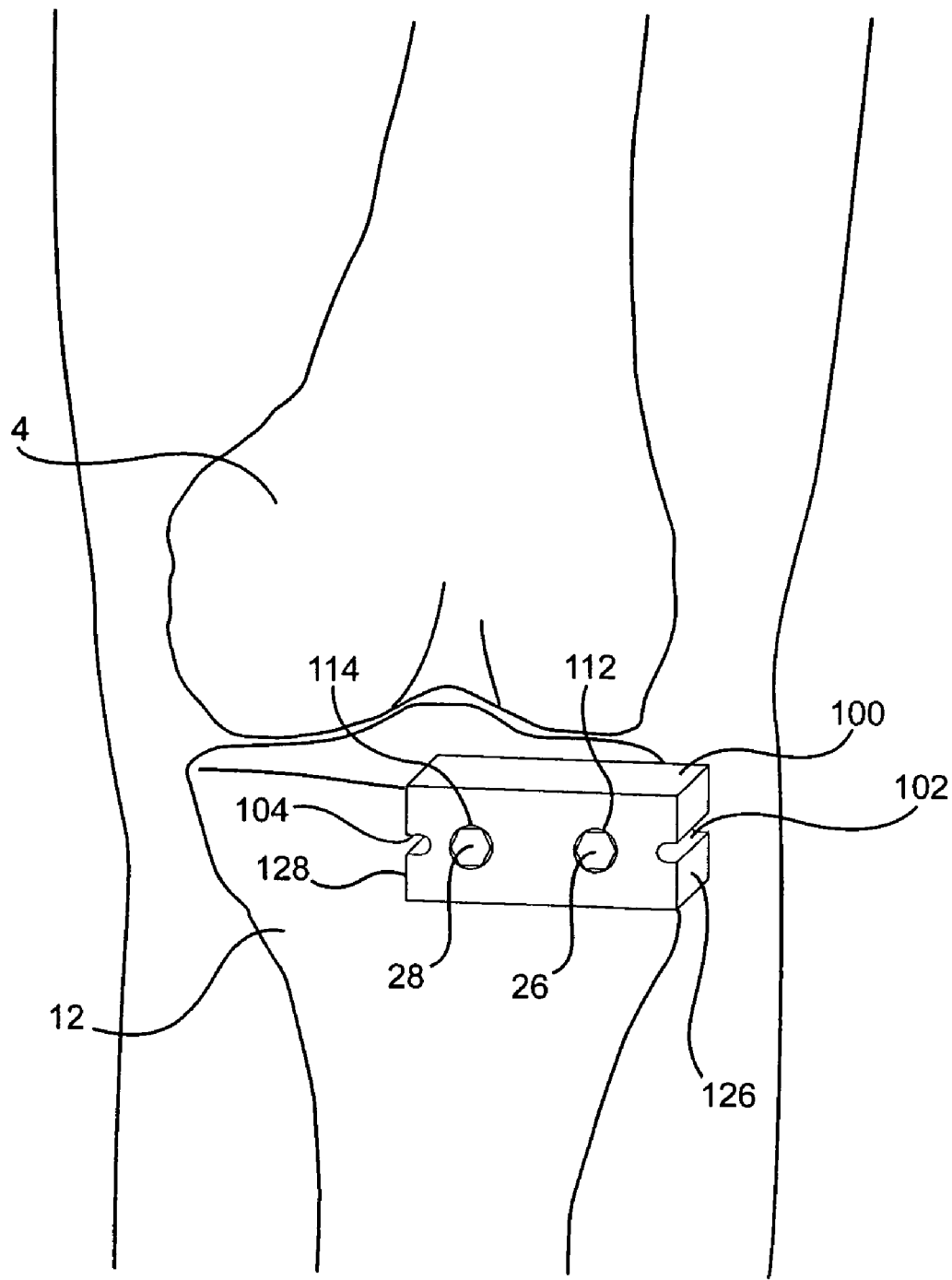
FIG. 12 a perspective view of a leg of a patient similar to FIG. 1 showing the tibia resection guide block situated over the two arthroscopic incisions with the guide pins received in the guide holes.
Figure 13:
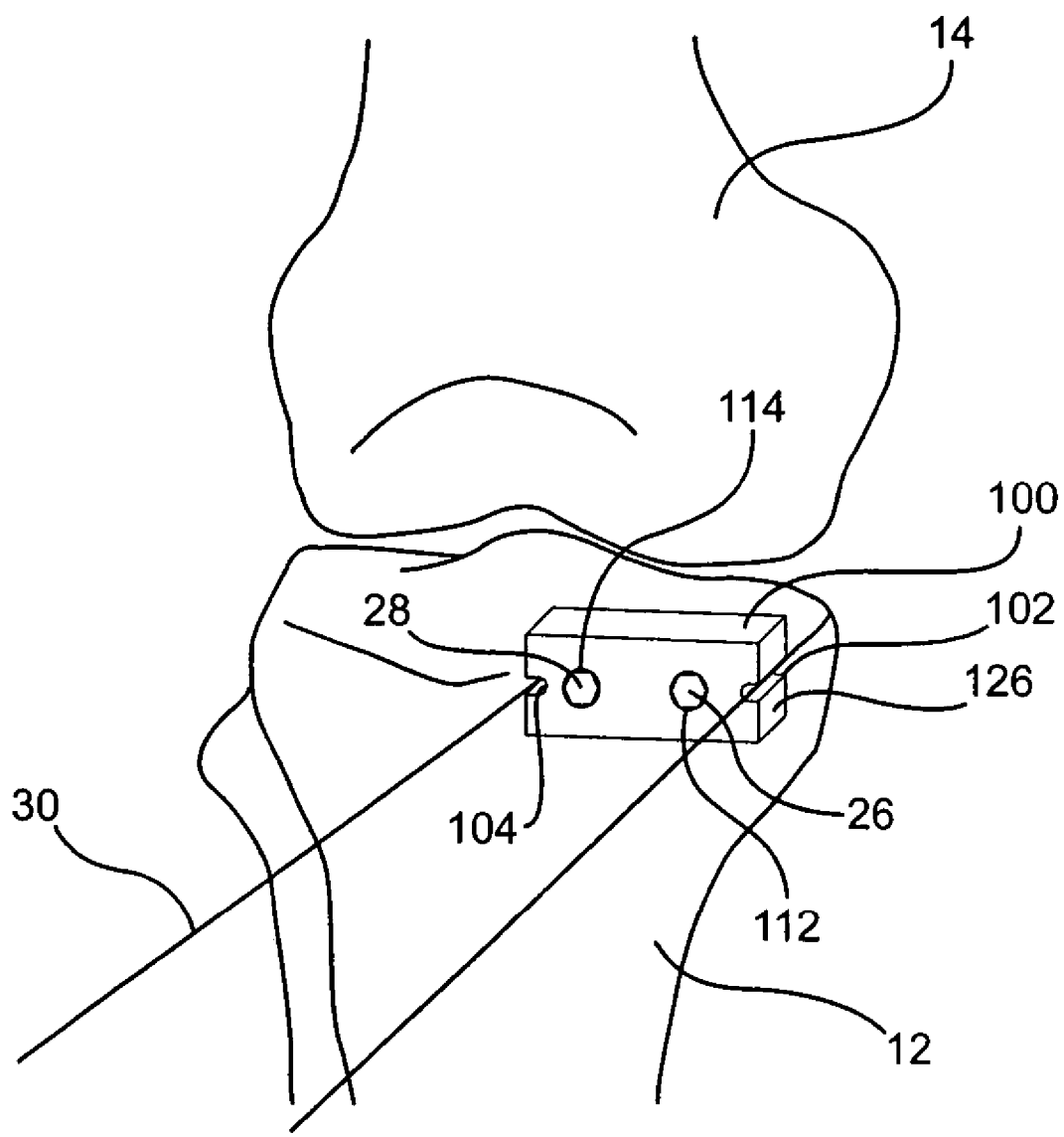
FIG. 13 is a perspective view of the leg of a patient similar to FIG. 12 with the skin and tissue surrounding the bone removed for clarity showing the wire saw after it has partially resected the medial portion of the proximal end of the tibia guided by the distal walls of the guide pins.
Figure 14:
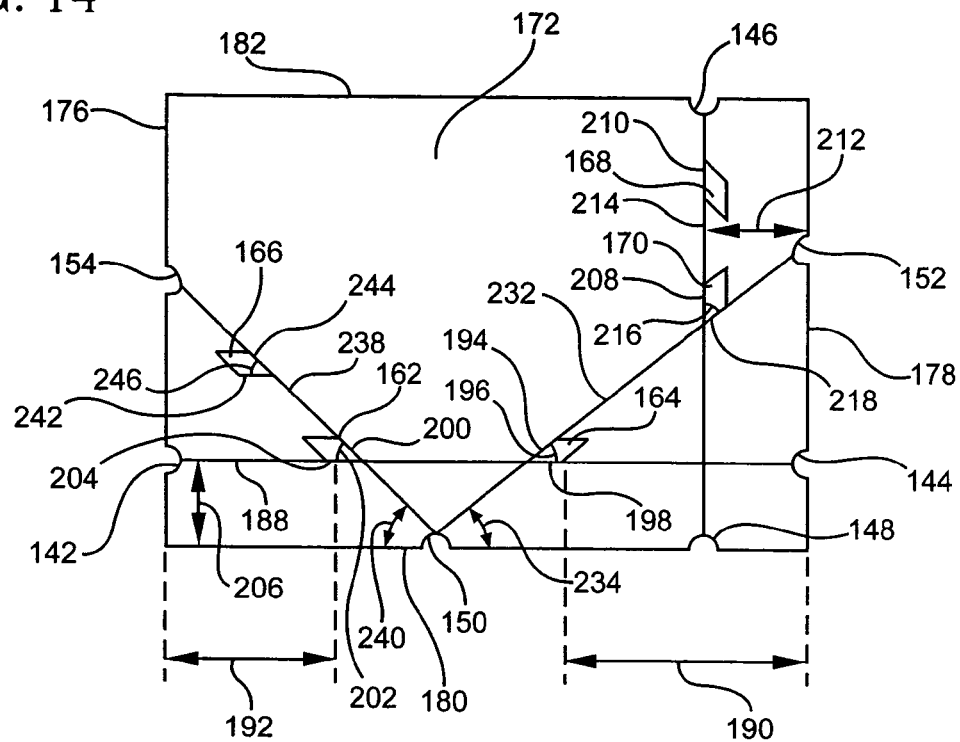
FIG. 14 is a medial elevation view of the medial face of a femur resection guide block including five guide holes for guiding the drilling of the femur and guiding the insertion of the alignment pins and seven guide slots configured to guide the wire saw along four resection planes.
Figure 15:
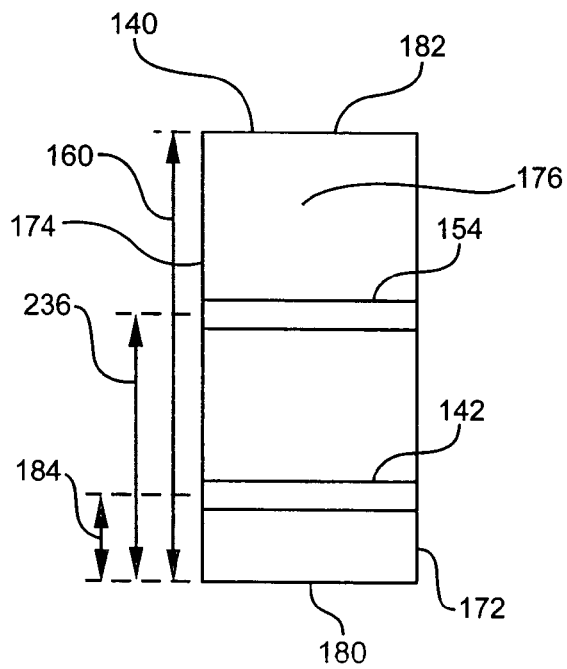
FIG. 15 is an anterior end view of the femur resection guide block of FIG. 14 showing the proximal anterior guide slot used to guide the wire saw during the anterior chamfer resection and distal anterior guide slot used to guide the wire saw during the distal resection and showing that both the proximal and distal anterior guide slots extend from the medial to the lateral wall parallel with the proximal and distal walls.
Figure 16:
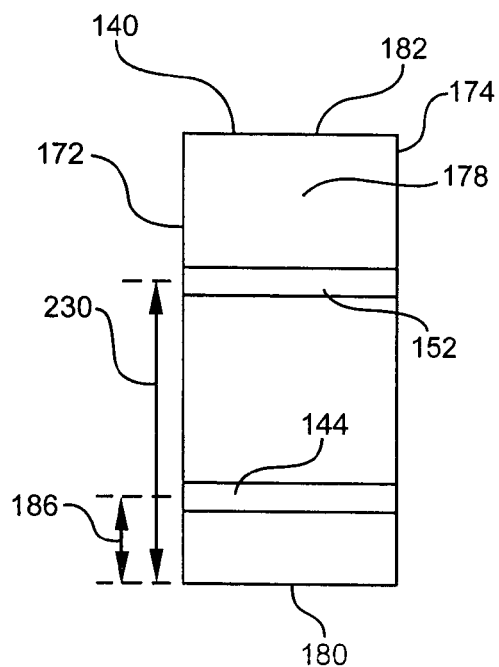
FIG. 16 is a posterior end view of the femur resection guide block of FIG. 14 showing the proximal posterior guide slot used to guide the wire saw during the posterior chamfer resection and distal posterior guide slot used to guide the wire saw during the distal resection and showing that both the proximal and distal posterior guide slots extend from the medial to the lateral wall parallel with the proximal and distal walls.
Figure 17:
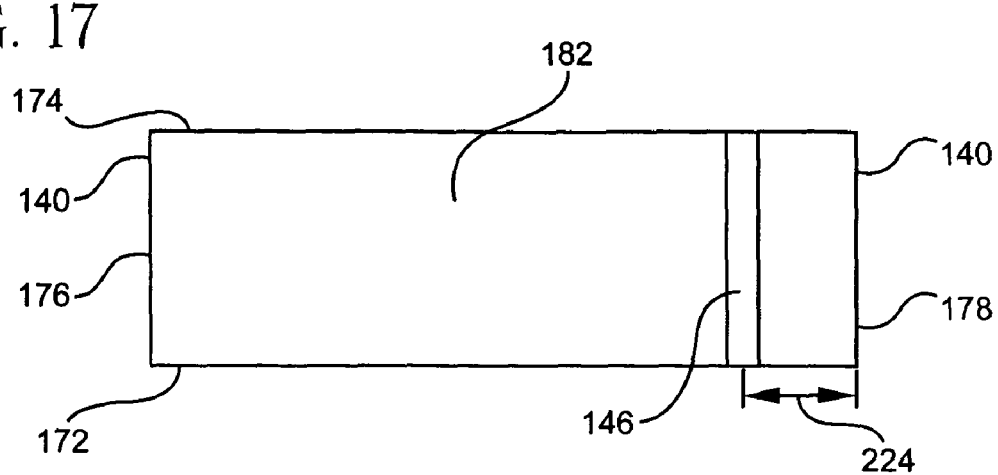
FIG. 17 is a proximal plan view of the femur resection guide block of FIG. 14 showing the posterior proximal guide slot used to guide the wire saw during the posterior resection and showing that the posterior proximal guide slot extends from the medial to the lateral wall parallel with the anterior and posterior walls.
Figure 18:
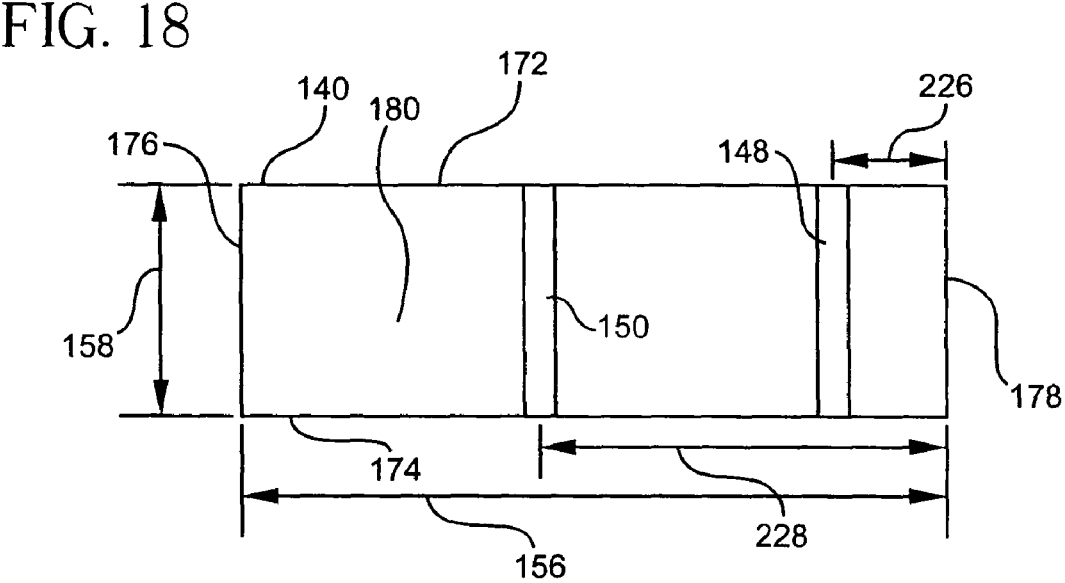
FIG. 18 is a distal plan view of the femur resection guide block of FIG. 14 showing the posterior distal guide slot used to guide the wire saw during the posterior resection and the chamfer distal guide slot used to guide the wire saw during both the anterior and posterior chamfer resections and showing that both the posterior and chamfer distal guide slots extends from the medial to the lateral wall parallel with the anterior and posterior walls.
Figure 19:
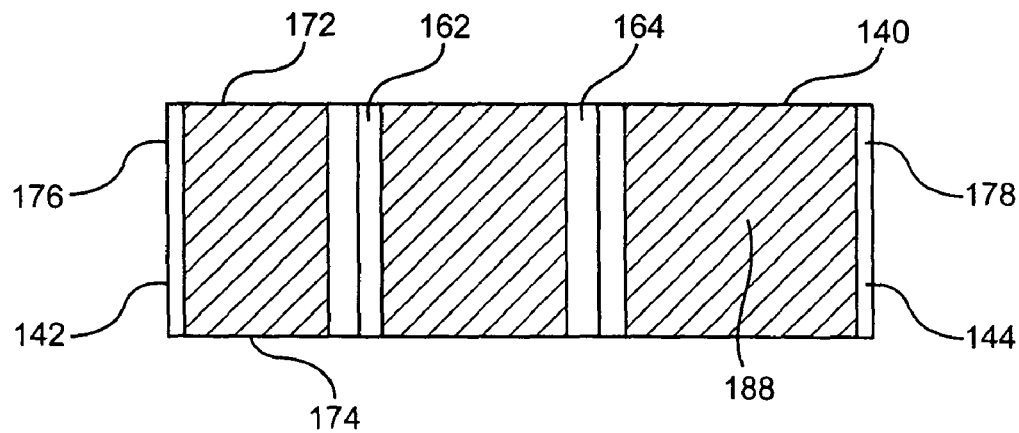
FIG. 19 is a sectional view of the femur resection guide block taken along line 19-19 of FIG. 14 which is along the reference plane of the distal resection showing that the centers of the distal posterior guide slot and the distal anterior guide slots align with the bottom walls of the distal anterior and distal posterior pin 64 holes.
Figure 20:
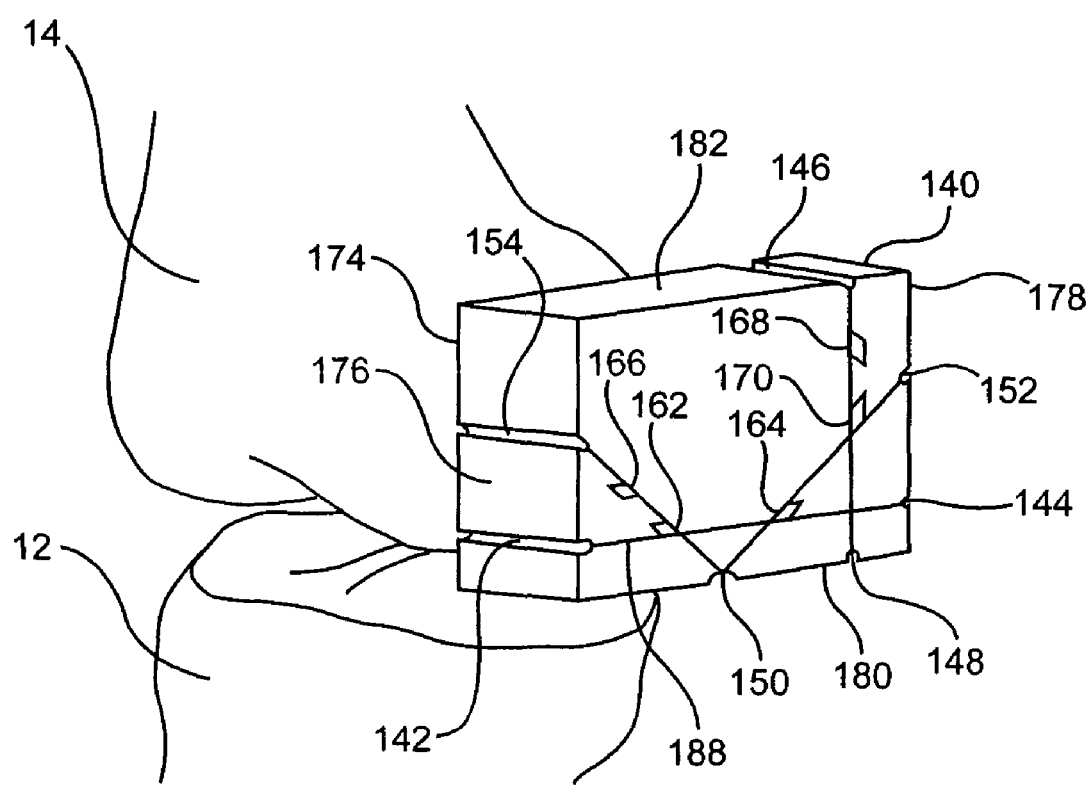
FIG. 20 is a perspective view of the leg of a patient similar to FIG. 13 with the skin and tissue surrounding the bone removed for clarity showing the femur resection guide block coupled to the femur with the guide pins received in the guide holes and extending through the femur to permit the wire saw to be used to resect the femur guided by the guide pins and the guide slots.
Figure 21:
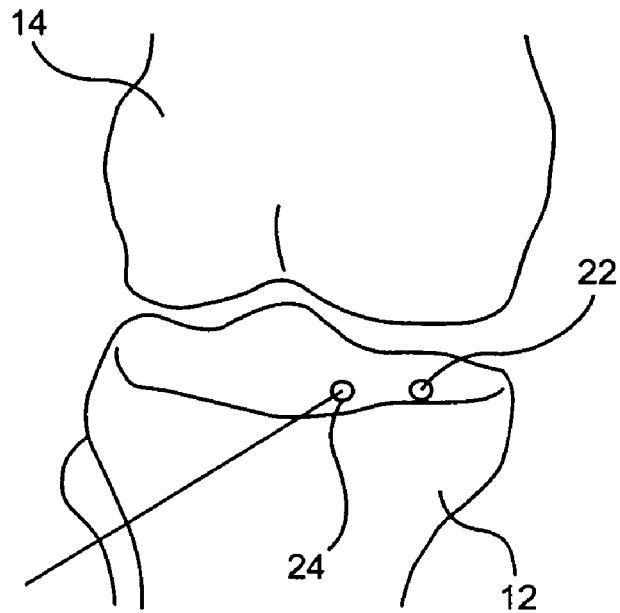
FIG. 21 is a perspective view of the leg of a patient with the skin and tissue surrounding the bone removed for clarity showing the anterior view of the femur and tibia and also showing two holes extending through the tibia to define a plane of resection and one end of the wire saw inserted through one of the guide holes.
Figure 22:
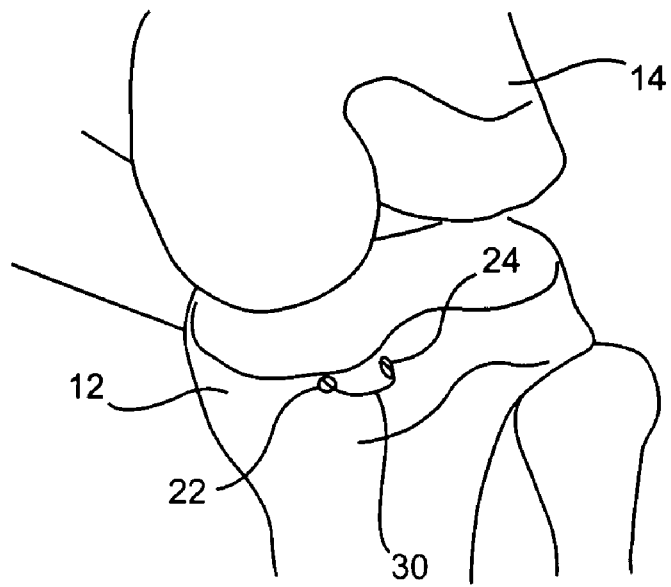
FIG. 22 is a posterior perspective view of the femur, fibula and tibia of the knee of a patient with the skin and tissue surrounding the bone removed for clarity showing a wire saw looped through two guide holes formed in the tibia to facilitate cutting the tibia in a plane defined by the guide holes.

As shown, for example, in FIG. 7, following the resection of the distal end of the femur 14, the wire saw 30 (not shown) is inserted through the arthroscopic incisions earlier utilized to drill the distal posterior pin hole 54 and the intermediate posterior pin hole 60 and through which the distal posterior pin 64 and the intermediate posterior pin 70 were inserted into the femur 14. The wire saw 30 is wrapped around the femur 14 to engage the anterior side 86 of the distal posterior pin 64 and the distal side 88 of the intermediate posterior pin 70. The wire saw 30 is oscillated to make a chamfer cut through the femur 14 guided by the anterior side 86 of the distal posterior pin 64 and the distal side 88 of the intermediate posterior pin 70 which define a metallic resection plane of reference 74 for a posterior chamfer resection. Following the posterior chamfer resection, the distal posterior pin 64 is left in the bone chip and the intermediate posterior pin 70 remains in the femur 14.

Next, the wire saw 30 (not shown) is inserted through the arthroscopic incisions made to drill the proximal posterior pin hole 58 and the intermediate posterior pin hole 60 and through which the proximal posterior pin 68 and the intermediate posterior pin 70 were inserted to wrap around the femur 14 and engage the anterior side 90 of the proximal posterior pin 68 and the anterior side 92 of the intermediate posterior pin 70. The wire saw 30 is then oscillated to resect the femur along the metallic resection plane of reference 76 (FIG. 8) defined by the anterior sides 90, 92 of the proximal posterior pin 68 and the intermediate posterior pin 70, respectively, to make a posterior resection. Both the proximal posterior pin 68 and the intermediate posterior pin 70 remain in the bone chip following the posterior resection.

Finally, the wire saw 30 is inserted through the arthroscopic incisions made to drill the proximal anterior pin hole 56 and distal anterior pin hole 52 and through which the proximal anterior pin 66 and distal anterior pin 62, respectively, were inserted to wrap around the femur 14 and engage the posterior side 94 of the proximal anterior pin 66 and the posterior side 96 of the distal anterior pin 62. The wire saw 30 is and oscillated to resect the femur 14 along the metallic resection plane of reference 78 (FIG. 9) defined by the posterior sides 94, 96 of the proximal anterior pin 66 and the distal anterior pin 62, respectively. Both the proximal anterior pin 66 and the distal anterior pin 62 remain in the bone chip following the anterior chamfer resection.

As shown for example, in FIGS. 10-13, a tibia alignment guide block 100 is provided to facilitate correct placement of the medial pin 26 and lateral pin 28 in the tibia 12 and to provide guide slots 102, 104 through which the wire saw 30 is to be oscillated during resection of the tibia 12. The tibia alignment guide block 100 has a width 106, a depth 108 and a height 110. While only a single tibia alignment guide block is shown, a plurality of different sized tibia alignment guide blocks are provided to facilitate utilization of a tibia alignment guide block for each of the plurality of different sized prosthesis which may be utilized. The surgeon selects the desired sized prosthesis based on the anatomy of the patient then utilizes the appropriately sized tibia alignment guide block 100 for the selected prosthesis.

Illustratively in a tibia alignment block 100 for a specific sized prosthesis, the width 106 is approximately one inch, the thickness is approximately one-half inches and the height is approximately one-half inches. The slots 102, 104 and pin alignment holes 112, 114 are formed to extend through the lateral axis 116 of the block 100 from the anterior face 118 to the posterior face 120. Two alignment holes 112, 114 are provided in the block 100 extending through the block parallel to the proximal surface 122 and distal surface 124 and the medial side surface 126 and lateral side surface 128. Illustratively, the center of the medial pin alignment hole 112 is displaced from the medial side surface 126 of the block 100 by a displacement 130 of approximately one-quarter inches. Similarly the lateral pin alignment hole 114 is displaced from the lateral side surface 128 of the block 100 by a displacement 132 of approximately one-quarter inches. Each pin alignment hole 112, 114 is sized to receive a guide pin 26, 28 (shown in this drawings as having a hexagonal cross-section) therethrough. Medial wire guide slot 102 is formed in the medial side surface 126 of the block guide 100 and extends parallel to the proximal surface 122 and distal surface 124 of the guide block 100. Lateral wire guide slot 104 is formed in the lateral side surface 128 of the guide block 100 and extends parallel to the proximal surface 122 and distal surface 124 of the guide block 100. A plurality of tibia alignment blocks 100 are provided in various sizes for use with various sized prosthesis provided for use in patients having various sized tibias 12.

In use, the surgeon or a member of the surgical team selects an appropriately sized tibia alignment block 100 based on the size of prosthesis selected based on the anatomy of the patient's tibia 12. The surgeon aligns the medial side surface 126 of the tibia alignment block 100 with the medial side of the patient's tibia 12 and presses the posterior surface 120 against the skin of the patient so that the pin alignment holes 112, 114 are positioned over an arthroscopic incisions 16, 18, respectively, in the patient's knee. The surgeon then selects a drill, or other instrument, appropriately sized to form a pin receiving hole 22, 24 in the patient's tibia 12. The drill is passed through one of the pin alignment holes (for purposes of description selected to be pin alignment hole 112) and maintained in the correct alignment by the hole 112 as the surgeon drills through the patient's tibia 12 to form pin hole 22. Once pin hole 22 is drilled in the tibia 12, alignment pin 26 is inserted through the pin alignment hole 112 and the pin hole 22 in the tibia 12 to aid in maintaining the position of the tibia alignment block 100 during the next drilling operation. The surgeon then passes the drill through the other pin alignment hole 114 which maintains the drill in the correct alignment as the surgeon drills pin hole 24 through the patient's tibia 12. The other pin 28 is then inserted through the other alignment hole 114 and through the pin hole 24 formed in the patient's tibia 12. Thus, the pin alignment holes 112, 114 help to ensure that the lateral and medial guide pins 26, 28 are inserted parallel to each other in the tibia 12 in the correct orientation.

The pins 26, 28 are of a sufficient length that they may extend completely through the tibia 12 in the location of the pin holes 22, 24 and extend out of the incisions 16, 18 and into the pin alignment holes 112, 114 when the tibia alignment block is held against the skin of the patient. Thus, the pins 26, 28 help to maintain the orientation of the alignment block 100 during the resection operation. The wire saw 30 is fished through the arthroscopic incisions 16, 18 and around the tibia 12 to engage the distal surfaces of the medial and lateral pins 26, 28. The portion of the wire saw 130 remaining outside of the patient is guided through the slots 102, 104 to be oscillated therein during resection of the tibia 12.

As shown, for example, in FIGS. 14-20, a femoral guide block 140 is provided to facilitate correct placement of the distal anterior, proximal anterior, distal posterior, proximal posterior and intermediate posterior pins 62, 64, 66, 68, 70 in the femur 14 and to provide guide slots 142, 144, 146, 148, 150, 152, 154 through which the wire saw 30 is to be oscillated during the four resection operations performed on the femur 14. Thus, the femur guide block includes five guide holes 162, 164, 166, 168, 170 and seven guide slots 142, 144, 146, 148, 150, 152, 154 (two for each resection operation to be performed, one of which is used for two different resection operations.) The five guide holes include to a distal anterior guide hole 162, a distal posterior guide hole 164, a proximal anterior guide hole 166, a proximal posterior guide hole 168 and an intermediate posterior guide hole 170. The seven guide slots include two distal resection guide slots 142, 144, a proximal and distal posterior resection guide slot 146, 148 a distal chamfer resection guide slot 150, a posterior chamfer resection guide slot 152 and an anterior chamfer resection guide slot 154.

The femoral guide block 140 has a medial surface 172, a lateral surface 174, an anterior surface 176, a posterior surface 178, a distal surface 180 and a proximal surface 182. Illustratively, each of the medial, lateral, anterior, posterior, distal and proximal surfaces 172, 174, 176, 178, 180, 182 are planar. The medial surface 172 and the lateral surface 174 are oppositely facing, spaced apart and parallel surfaces with the anterior, posterior, distal and proximal surfaces 176, 178, 180, 182, respectively, extending perpendicularly between the two. Thus anterior surface 176 and posterior surface 178 are also oppositely facing, spaced apart and parallel surfaces as are the distal and proximal surfaces 180, 182. The femoral guide block 140 has a width 156, a depth 158 and a height 160. A plurality of femoral guide blocks 140 are provided sized to be utilized with the plurality of prosthesis provided for use with patients having varying femoral anatomies. Illustratively in a femoral guide block for a specific prosthesis, the width 156 is approximately two inches, the depth 158 is approximately one-half inches and the height 160 is approximately one and a half inches.

The anterior distal resection guide slot 142 is formed in the anterior surface 176 and extends from the medial face 172 to the lateral face 174 parallel with the proximal surface 182 and distal surface 180 of the block 140. The center of the anterior distal guide slot 142 is displaced from the distal surface 180 of the block 140 by a displacement 184, which in the specific femoral guide block 140 described herein is approximately one-quarter inches. The posterior distal resection guide slot 144 is formed in the posterior surface 178 and extends from the medial surface 172 to the lateral surface 174 parallel with the proximal surface 182 and distal surface 180 of the block 140. The center of the posterior distal guide slot 144 is displaced from the distal surface 180 of the block 140 by a displacement 186, which in a specific femoral guide block 140 described herein is approximately one-quarter inches. Thus, anterior and posterior distal guide slots 142, 144 define a plane 188 parallel to and displaced from the distal surface 180 of the block 140. Illustratively, each of the anterior and posterior distal guide slots 142, 144 has a semicircular-shaped cross section to facilitate the wire saw 130 riding therein during oscillatory movement resulting in resection of the femur 14.

The distal anterior alignment hole 162 and distal posterior alignment hole 164 extend through the block 140 from the medial surface 172 to the lateral surface 174 parallel to the proximal surface 182 and distal surface 180 and the anterior surface 176 and posterior surface 178. Illustratively, the center of the distal posterior guide pin alignment hole 164 is displaced anteriorly from the posterior surface 178 of the block 140 by a displacement 190 of approximately three-quarter inches. Similarly the center of the distal anterior guide pin alignment hole 162 is displaced posteriorly from the anterior surface 176 of the block 140 by a displacement 192 of approximately one-half inches.

The distal anterior and distal posterior pin alignment holes 162, 164 are each sized to receive a guide pin 62, 64 therethrough. In the illustrated embodiment, the distal posterior guide pin hole 164 and the distal anterior guide pin hole 162 each has a cross section conforming to the cross section of the distal posterior guide pin 64 and distal anterior guide pin 62, respectively, i.e the holes have a parallelogram cross section. The anterior side wall 194 of the distal posterior guide hole 164 forms an angle 196 with the distal wall 198 that is equal to the desired angle of the posterior chamfer cut. The posterior side wall 200 of the distal anterior guide hole 162 forms an angle 202 with the distal wall 204 that is equal to the desired angle of the anterior chamfer cut. The distal wall 204 of the distal anterior guide hole 162 and the distal wall 198 of the distal posterior guide hole 164 are each parallel to the distal surface 180 and are each displaced from the distal surface 180 of the guide block by a displacement 206 equal to the displacement 184, 186 of the centers of the anterior and posterior distal resection guide slots 142, 144, respectively, from the distal surface 180. In the illustrated guide block 140 the displacement 206 is approximately one-half inches. Thus, the distal rescission guide slots 142, 144 and the distal walls 202, 198 of the distal anterior and distal posterior guide holes 162, 164, respectively, lie in a common plane parallel 188 to the proximal and distal surfaces 182, 180 of the block 140.

The intermediate posterior guide pin hole 170 and the proximal posterior guide pin hole 168 extend through the block 140 from the medial surface 172 to the lateral surface 174 parallel to the proximal and distal surfaces 182, 180 and the anterior and posterior surfaces 176, 178. Illustratively, the anterior wall 208 of the intermediate posterior guide pin alignment hole 170 and the anterior wall 210 of the proximal posterior guide pin hole 168 are parallel to the posterior surface 178 and are each displaced anteriorly from the posterior surface 178 of the block 140 by a displacement 212 of approximately one-quarter inches. Thus, the anterior walls 208, 210 of the intermediate posterior hole 170 and the proximal posterior hole 168 lie in a plane 214 parallel to the posterior surface 178.

The intermediate posterior and proximal posterior pin alignment holes 170, 168 are each sized to receive a guide pin 70, 68 therethrough. In the illustrated embodiment, the intermediate posterior and proximal posterior guide pin holes 170, 168 have a cross section conforming to the cross section of the intermediate posterior and proximal posterior guide pins 70, 68, respectively, i.e the holes 170, 168 have a parallelogram cross section. The anterior side wall 208 of the intermediate posterior guide hole 170 forms an angle 216 with the distal wall 218 that is equal to the compliment of the desired angle of the posterior chamfer cut.

The proximal posterior resection guide slot 146 is formed in the proximal surface 182 and extends from the medial surface 172 to the lateral surface 174 parallel with the posterior and anterior surfaces 178, 176 of the block 140. The distal posterior resection guide slot 148 is formed in the distal surface 180 and extends from the medial surface 172 to the lateral surface 174 parallel with the posterior and anterior surfaces 178, 176 of the block 140. The center of the proximal posterior resection guide slot 146 is displaced from the posterior surface 178 of the block by a displacement 224, which in the specifically described femoral guide block 140 is approximately one quarter inches. The center of the distal posterior guide slot 148 is displaced from the posterior surface 178 of the block 140 by a displacement 226, which in a specifically described femoral guide block 140 is approximately one quarter inches. Thus, proximal and distal posterior distal guide slots 146, 148 define a plane 214 parallel to and displaced from the posterior surface 178 of the block 140. Illustratively, each of the proximal and distal posterior guide slots 146, 148 has a semicircular-shaped cross section to facilitate the wire saw 230 riding therein during oscillatory movement resulting in resection of the femur 14. The centers of the proximal and distal posterior guide slots 146, 148 and the anterior walls 208, 210 of the intermediate posterior guide hole 170 and the proximal posterior guide hole 168, respectively, lie in the same plane 214. Thus, displacements 212, 224, 226 are all equal.

The distal chamfer resection guide slot 150 is formed in the distal surface 180 and extends from the medial surface 172 to the lateral surface 174 parallel with the posterior and anterior surfaces 178, 176 of the block 140. The posterior chamfer resection guide slot 152 is formed in the posterior surface 178 and extends from the medial surface 172 to the lateral surface 174 parallel with the proximal and distal surfaces 182, 180 of the block 140. The center of the distal chamfer resection guide slot 150 is displaced from the posterior surface 178 of the block 140 by a displacement 228, which in described femoral guide block 140 is approximately one and one quarter inches. The center of the posterior chamfer resection guide slot 152 is displaced from the distal surface 180 of the block by a displacement 230, which in the described femoral guide block 140 is approximately one and one quarter inches. Thus, distal chamfer resection guide slot 150 and the posterior chamfer resection guide slot 152 define a plane 232 forming an angle 234 with the distal surface 180 of the block 140. In the illustrated embodiment the angle 234 is forty-five degrees, the same as the desired angle of resection of the femur 14 during the posterior chamfer resection. Illustratively, each of the distal chamfer guide slot 150 and the posterior chamfer guide slot 150 has a semicircular-shaped cross section to facilitate the wire saw 130 riding therein during oscillatory movement resulting in resection of the femur 14. The centers of the distal chamfer guide slot 150 and the posterior chamfer guide slot 150, the anterior wall 194 of the posterior distal pin hole 164 and the distal wall 218 of the intermediate posterior guide hole 170 lie in the same plane 232.

The distal chamfer resection guide slot 150 also serves as a guide for the anterior chamfer resection along with the anterior chamfer resection guide slot 154. The anterior chamfer resection guide slot 154 is formed in the anterior surface 176 and extends from the medial surface 172 to the lateral surface 174 parallel with the proximal and distal surfaces 182, 180 of the block 140. The center of the anterior chamfer resection guide slot 154 is displaced from the distal surface 180 of the block 140 by a displacement 236, which in a described femoral guide block 140 is approximately three-quarter inches. Thus, distal and anterior chamfer resection guide slots 150, 154 define a plane 238 forming an angle 240 with the distal surface 180 of the block 140. In the illustrated embodiment the angle 240 is forty-five degrees, the same as the desired angle of resection of the femur 14 during the anterior chamfer resection. Illustratively, each of the anterior chamfer guide slot 154 has a semicircular-shaped cross section to facilitate the wire saw 30 riding therein during oscillatory movement resulting in resection of the femur 14.

The proximal anterior guide hole 166 extends through the block 140 from the medial surface 172 to the lateral surface 174 parallel to the proximal and distal surfaces 182, 180 and the anterior and posterior surfaces 176, 178. Illustratively, the distal wall 242 of the proximal anterior guide hole 166 is parallel to the distal surface 180. The proximal anterior guide hole 166 is sized to receive a guide pin 66 therethrough. In the illustrated embodiment, the proximal anterior guide hole 166 has a cross section conforming to the cross section of the proximal anterior guide pin 66, i.e the hole 166 has a parallelogram cross section. The posterior wall 244 of the proximal anterior guide hole 166 forms an angle 246 with the distal wall 242 that is equal to the desired angle of the anterior chamfer cut. The centers of the distal and anterior chamfer guide slots 150, 154, the posterior wall 244 of the proximal anterior guide hole 166 and the posterior wall 200 of the distal anterior guide hole 162 lie in the same plane 238.

In use, the surgeon or a member of the surgical team selects an appropriately sized femoral guide block 140 based on the size of the prosthesis selected for insertion into the patient's femur 14. The surgeon aligns the anterior surface 176 of the femoral guide block 140 with the patient's femur 14 so as to produce bone cuts in the planned planes. The planned planes can be determined by a computer or through the use of alignment rods. The pin alignment holes 162, 164, 166, 168, 170 are positioned over arthroscopic incisions in the patient's knee. The surgeon then selects a drill, or other instrument, appropriately sized to form a pin-receiving hole 52, 54, 56, 58, 60 in the patient's femur 14. The drill is passed through a pin alignment hole 162, 164, 166, 168, 170 (selected as pin alignment hole 162 for purposes of description) and maintained in the correct alignment by the hole 162 as the surgeon drills through the patient's femur 14.

Once a hole 52 is drilled in the femur 14, a temporary round alignment pin may be inserted through the pin alignment hole 162 and the hole 52 in the femur 14 to aid in maintaining the position of the femoral guide block 140 during the next drilling operation.

The surgeon then passes the drill through another pin alignment hole (selected for purposes of description and pin alignment hole 164) which maintains the drill in the correct alignment as the surgeon drills through the patient's femur 14. Another temporary round pin is then inserted through the second alignment hole 164 and through the second hole 54 formed in the patient's femur 14. The first and second temporary round pins maintain the femoral guide block 140 in the correct position during drilling of the remaining three holes 56, 58, 60. Each of the remaining three holes 56, 58, 60 is drilled through the appropriate alignment pin hole 166, 168, 170.

If parallelogram shaped alignment pins 62, 64, 66, 68, 70 are to be utilized, they may be driven through the parallelogram shaped alignment holes 162, 164, 166, 168, 170, respectively, and the drilled holes 52, 54, 56, 58, 60, respectively, in the femur 14 instead of round temporary alignment pins. Otherwise, the remaining three drilled holes 56, 58, 60 may be reamed with parallelogram shaped reamers following each drilling step. Once the remaining three pins 66, 68, 70 are placed through the remaining three alignment holes 166, 168, 170 and the drilled or drilled and reamed holes 56, 58, 60, each of the first two temporary round alignment pins may be removed so that the drilled holes 52, 54 may be reamed through the appropriate alignment hole 162, 164, respectively, with the appropriately configured reamer. Following reaming, parallelogram cross section pins 62, 64 are inserted into the first two alignment holes 162, 164, respectively, and the drilled and reamed holes 52, 54, respectively, to aid in holding the femur guide block 140 in proper alignment during the resection operations. Thus, the pin alignment holes 162, 164, 166, 168, 179 help to ensure that the guide pins 62, 64, 66, 68, 70 are inserted parallel to each other in the femur 14 in the correct orientation. Those skilled in the art will recognize that the order of hole forming and pin insertion can be modified and that pins may be driven into the femur without prior formation of a hole within the scope of the disclosure.

The pins 62, 64, 66, 68, 70 also help to maintain the orientation of the alignment block 140 during the resection operations. The wire saw 30 is fished through the appropriate arthroscopic incisions and around the femur 14 to engage the appropriate surfaces of the appropriate pins for each resection operation. The portion of the wire saw 30 remaining outside of the patient is guided through the appropriate resection guide slots 142, 144, 146, 148, 150, 152, 154 to be oscillated therein during resection of the femur 14.

The disclosed method could also work without a femoral alignment block 140. A computer can be used to guide a drill into the correct orientation to drill holes 52, 54, 56, 58, 60 through the femur 14. A plurality of pins 62, 64, 66, 68, 70 inserted with a computer guided tool can perform the same function as the illustrated block 140.

As shown, for example, in FIG. 25-28, an adapter tool 250 is provided to power a wire cutting saw 252 for making bone cuts between two pins, shown for illustration purposes as tibia guide pins 26, 28. The adapter tool 250 includes a drive shaft 254 coupled to an adapter body 256 formed concentrically about a longitudinal axis 258. The drive shaft 254 is adapted for coupling to a drill that can be used to drive the adapter body 256 into the bone. The adapter body 256 is formed to include a cylindrical side wall 260, a distal end wall 262 and a cylindrical pin-receiving cavity 264 formed concentrically about the longitudinal axis 258. The distal end wall 262 of adapter body 256 is configured to act as a cutting face formed to include teeth 266 to enable the adapter 250 to cut through the bone when driven by a drill. The cylindrical pin-receiving cavity 264 extends longitudinally into the adapter body 256 from the distal end wall 262 which is acting as a cutting face and is sized to receive an alignment pin 26, 28 therein. Thus, the adapter body 256 is configured to be guided by a pin 26, 28 inserted into the pin-receiving cavity 264 as it is drilling through the bone.

The adapter body 256 is also configured to drive the wire saw 252. Adjacent the cutting face 262, a circumferential groove 268 is formed in the cylindrical side wall 260 of the adapter body 256. The circumferential groove 268 includes a rearwardly slanted proximal wall 270 a forwardly slanted distal wall 272 and a driving wall 274. Circumferential groove 268 is configured to act as a pulley within which a looped wire cutting saw 252 may ride.

Figure 26:
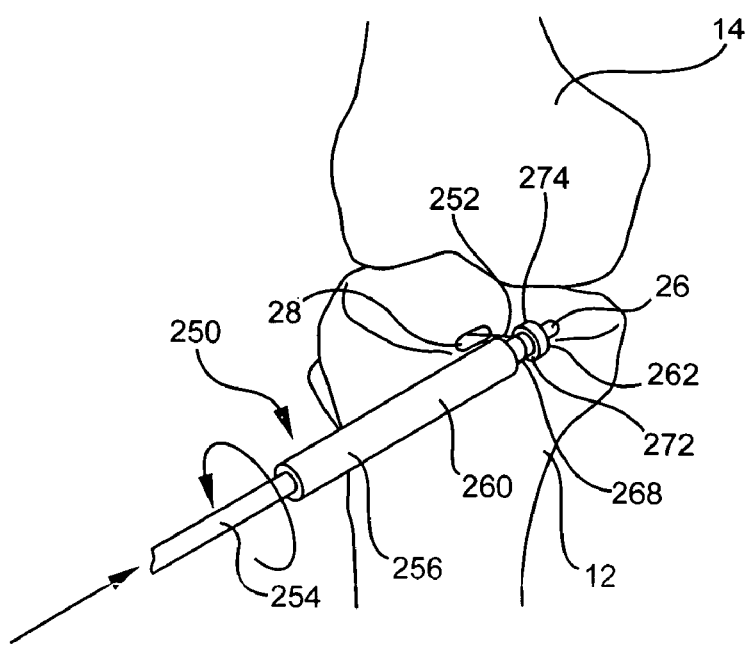
FIG. 26 is a perspective view of the femur and tibia of the knee of a patient showing the adapter tool guided over the medial guide pin and driving a looped wire saw guided by the adapter tool and the lateral guide pin so that the adapter tool and wire saw can be advanced into the tibia to accomplish a resection along the plane defined by the medial and lateral guide pins.
Figure 27:
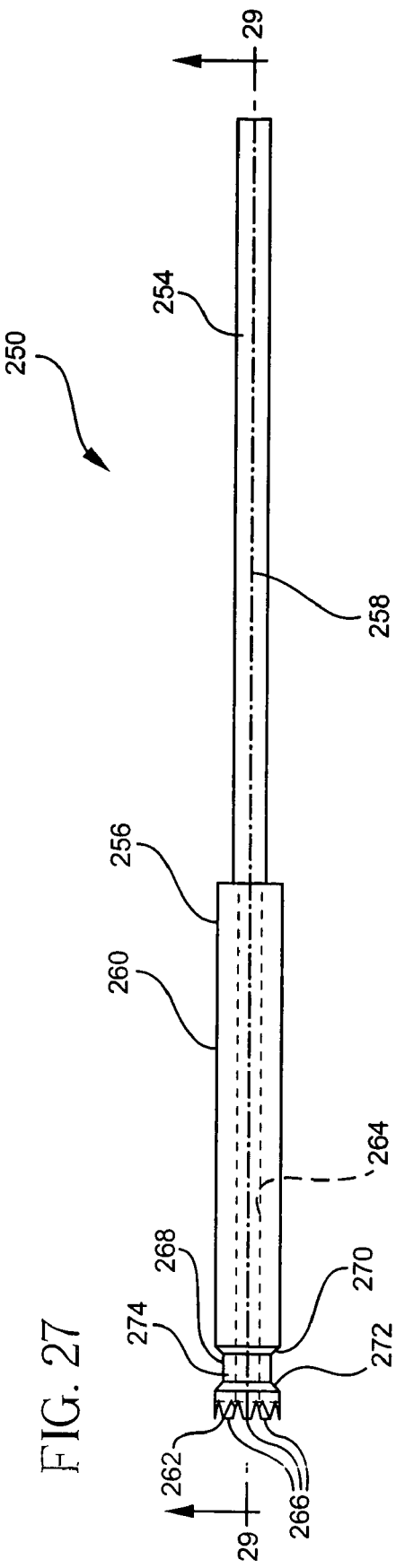
FIG. 27 is a plan view of the adapter tool of FIG. 25.
Figure 28:
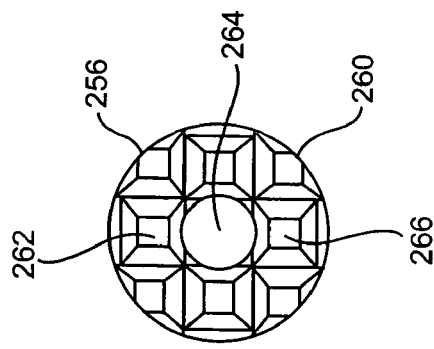
FIG. 28 is a distal end view of the adapter tool of FIG. 25.
Figure 33:
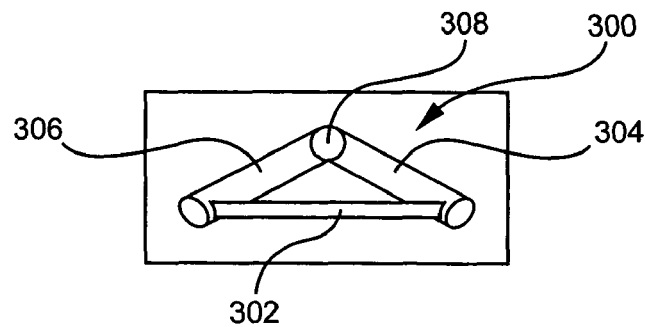
FIG. 33 is a distal end elevation view of the wire saw and wire saw holder of FIG. 31; and, FIG. 34 is a sectional view of a wire saw and wire saw holder with mechanically retractable fingers showing a retractable finger pivotally mounted to a stationary finger and an actuator mounted for reciprocal movement within the stationary finger forming a rack and pinion arrangement with the retractable finger and showing the retractable finger in the retracted position in phantom lines.

As shown, for example, in FIG. 26, the adapter 250 and a looped wire saw 252 is shown being used to resect a section of the proximal tibia 12 between lateral guide pin 28 and medial guide pin 26 (shown here as round pins) inserted in the tibia 12 as described above. In the illustrated embodiment, the looped wire saw 252 is tensioned around the adapter body 250 and the lateral pin 28. The medial pin 26 is inserted into the pin-receiving cavity 264 in the adapter body 256 to guide the adapter 250 as it is driven through the bone while being rotated about the longitudinal axis 258 by a drill (not shown). The looped wire saw 252 rides in circumferential groove 268 frictionally engaging the driver surface 274 of the adapter body 256 and on the lateral pin 28 and is driven by the adapter body 256 as it rotates. The side walls 270, 272 of the circumferential groove 270 act to prohibit the tensioned wire saw 252 from sliding forwardly or rearwardly. When the adapter 250 is rotated about its longitudinal axis 258 it can be fed into the tibia 12 guided by the medial pin 26. As the adapter body 256 advances into the tibia 12, so does the wire saw 252. The adapter body 156 and the wire saw 252 cut a chip out of the tibia 12 between the lateral and media pins 28, 26.

While described as being utilized with a wire cutting saw 252, the disclosed guided adapter 250 can also be utilized to drive a chain saw or other cutting tool within the scope of the disclosure.

As shown, for example, in FIG. 30-33, a saw oscillating tool 300 is provided to improve the efficiency of a wire saw when utilized with the alignment guide pins described above. The saw oscillating tool 300 comprises a short wire saw 302 that is tensioned between two fingers 304, 306 extending from a shaft 308 when the fingers 304, 306 are in an extended position as shown, for example, in solid lines in FIGS. 30-33. The fingers 304, 306 are retractable to a retracted position, as shown, for example, in phantom lines in FIG. 31. In the first illustrated embodiment of saw oscillating tool 300, both of the fingers 304, 306 are formed from shape memory alloy, such as Nickel Titanium Naval Ordinance Laboratory (NITINOL) alloy. The shape memory phenomenon is utilized to extend and retract the fingers 304, 306. It is within the scope of the disclosure for only one of the fingers 304, 306 to be formed from shape memory alloys.

Figure 34:
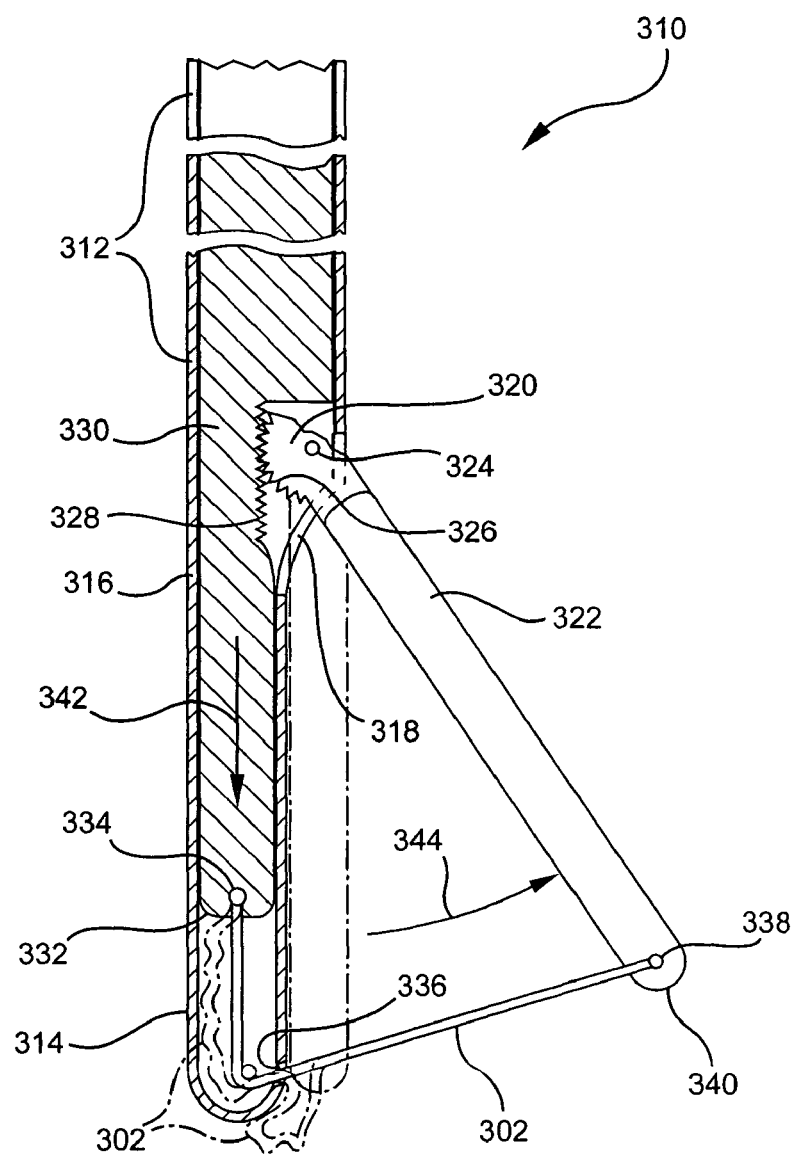

A second embodiment of saw oscillating tool 310 is shown in cross-section in FIG. 34. Saw oscillating tool 310 includes an outer hollow body 312 tapering toward the distal end 314 to form a finger 316. A slot 318 is formed in the hollow body 312 adjacent the taper. The slot 318 is sized to receive the proximal end 320 of a retractable finger 322 therein. Retractable finger 322 is coupled for pivotal movement relative to the hollow body 312 about a pivot pin 324. The proximal end 320 of the retractable finger 322 is formed to include a pinion gear 326 formed about the pivot axis 324. The pinion gear 326 cooperates with a rack gear 328 formed on an inner shaft 330 configured to slide longitudinally within the hollow body 312. The distal end 332 of the inner shaft 330 is coupled to one end 334 of the wire saw 302 which extends through a hole 336 adjacent the distal end 314 of finger 316. The wire saw 302 is coupled at the other end 338 to the distal end 340 of the retractable finger 322. As the inner shaft 330 is slid distally in the direction of arrow 342 within the hollow body 312, the rack and pinion gears 328, 326 cooperate to induce the retractable finger 322 to rotate in the direction of arrow 344 to the extended position as shown, in solid lines, in FIG. 34.

As shown, in phantom lines, in FIG. 34, when the retractable finger 322 is in the retracted position, it lies along side finger 316. Some slack is present in the wire saw 302. That slack may be gathered within the finger 316 prior to extension of the retractable finger 322, as shown, in FIG. 34. Locking pins and holes may be provided in the hollow body 312 and sliding inner shaft 330 to lock the sliding inner shaft in a position that locks the retractable finger 322 in the extended position. It is within the scope of the disclosure for other appropriate mechanisms, such as those used in laparoscopy scissors to be utilized to extend and retract fingers of an arthroscopic saw oscillating tool.

The saw oscillating tools 300, 310 attach to the chuck 350 of an oscillatory power tool (not shown) in a similar manner, as shown, for example, in FIG. 30 with respect to tool 300. Prior to insertion of the saw oscillating tool into an arthroscopic incision, the retractable finger or fingers are in the retracted position so that the tool presents a minimal cross section. Once the saw 302 and fingers are inserted into the arthroscopic incision, the retractable finger or fingers are extended so that the saw is tensioned between the fingers. The wire cutting saw 302 is be positioned against guide pins (such as 26, 28) inserted in the bone as described above to guide the saw 302 during resection of the bone. The oscillatory power tool is then used to induce an oscillatory motion into the wire cutting saw 302 which may then be used to cut the bone by guiding the saw along the guide pins as the tool 300, 310 is urged toward the bone. While described as utilizing an oscillatory power tool, it is also within the scope of the disclosure to use a rotary drill and a mechanical coupling to produce the oscillatory power.

An alternative method of bone preparation is shown for example, in FIGS. 21-24. Holes 22, 24 are drilled through the bone, shown as the tibia 12, to define a resection plane in the same manner as described above. However, rather than inserting pins in the hole 22, 24 to act as a guide for resection along the resection plane, the wire saw 30 is threaded through the holes 22, 24 and the walls of the holes 22, 24 are used to guide resection along the resection plane. It is within the scope of the disclosure for a guide tool, such as those disclosed above, to aid in pulling the wire saw 30 through the holes 22, 24 in an arthroscopic manner.

Figure 23:
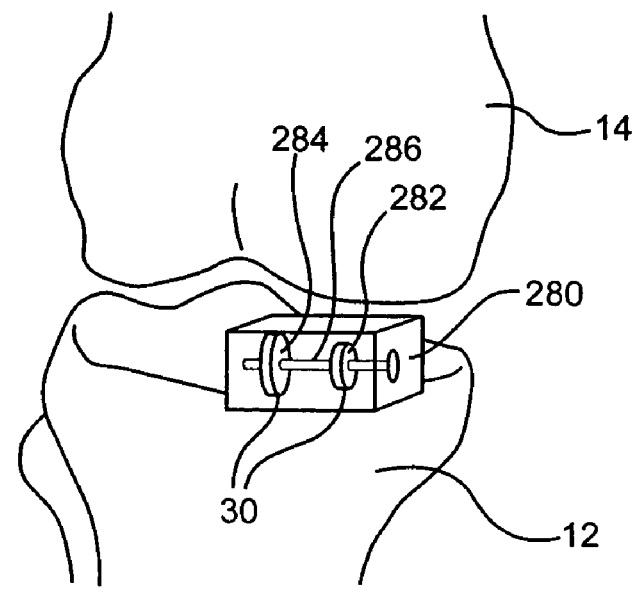
FIG. 23 is a anterior perspective view of the knee of a patient similar to FIG. 21 showing a guide tool and power adapter for facilitating cutting through the tibia arthroscopically with the wire saw, the power adapter includes a drive shaft with a large wire saw collecting pulley and a smaller wire saw dispensing pulley.
Figure 24:
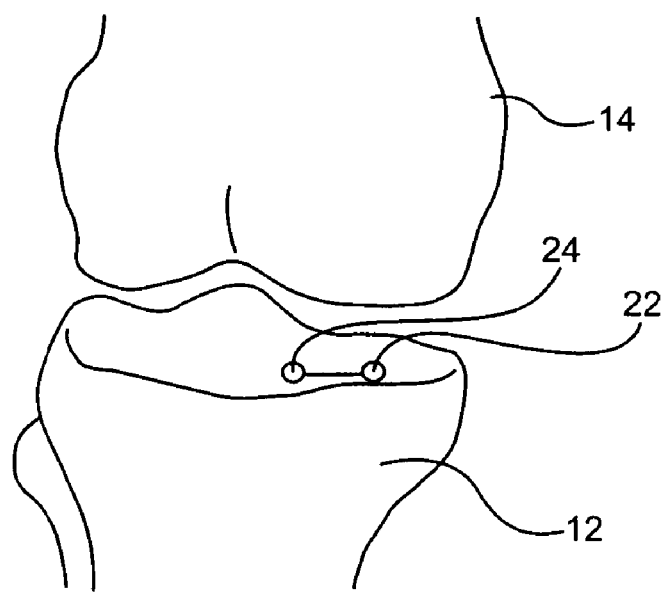
FIG. 24 is a posterior perspective view of the knee of the patient showing the tibia with a cut therein along the plane defined by the guide holes.
Figure 25:
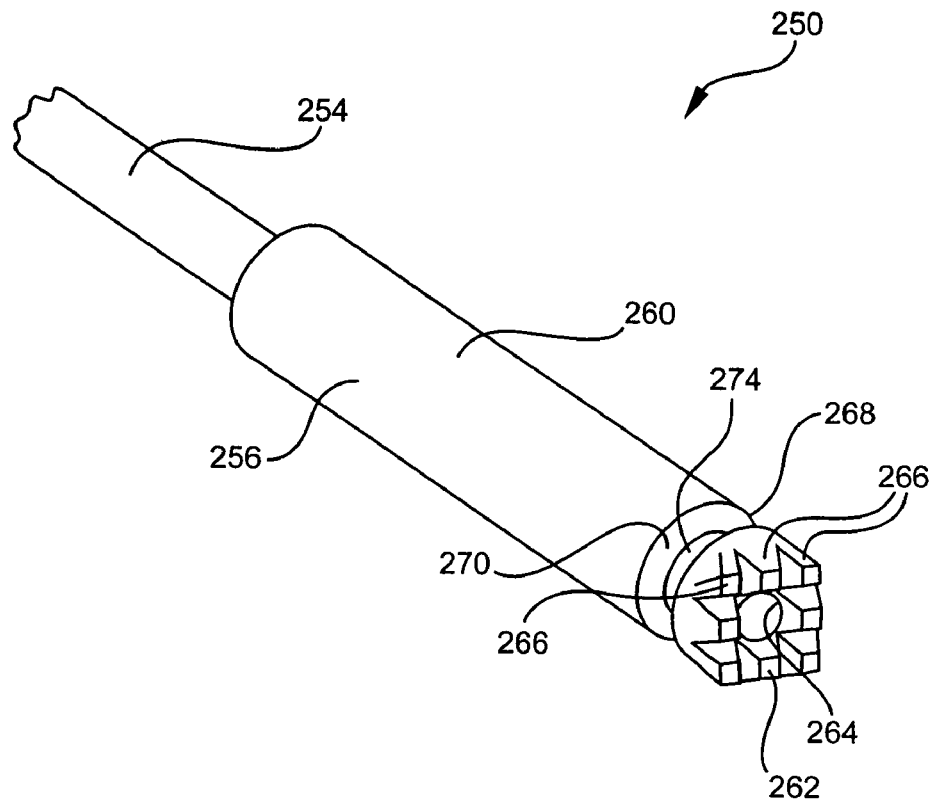
FIG. 25 is a perspective view of a portion of an adapter tool to be guided by one pin extending through a bone while driving a wire saw guided by the adapter tool and a second pin extending through the bone to cut the bone along a plane defined by the pins.

A power adapter 280 is shown in FIG. 23 to aid in pulling the wire saw 30 through the bone along the resection plane. The adapter 280 comprises two pulleys 282, 284 on a single drive shaft 286. The wire saw is initially wound about the feed pulley 282. Sufficient amounts of the wire saw 30 are fed out from the feed pulley to allow the wire saw 30 to be passed through the holes 22, 24 formed in the tibia 12 and for the end to be coupled to the uptake pulley 284. The feed pulley 282 is smaller than the uptake pulley 284. Thus, as the drive shaft 286 turns, the length of the looped wire saw 30 shortens as it cuts through the bone. The illustrated method and device can be used to make a single cut along a resection plane in a bone that does not remove a bone chip, as shown, for example, in FIG. 24.

A second cut could be made in a similar fashion to remove the bone chip. Additionally, this cut could be made using one hole and a slot carved into the side of the bone. When a slot is carved into the side of the bone to act as a resection guide, a burr may be left extending downwardly from the upper wall of the slot. The wire saw is then guided through the hole and the slot to resect the bone.

This disclosed devices and methods facilitate truly arthroscopic bone preparation. The advantages to the patient may be extensive. One would expect faster recovery, less pain, better quadriceps function, smaller scars, and shorter hospital stays. The patient would be expected to return to work faster and have higher function upon return to work. Also, one would expect lower morbidity and infection rates. The instrumentation described is simple to manufacture and may propose huge cost savings for both orthopaedic manufacturer and the hospital.

Although specific embodiments of the invention have been described herein, other embodiments may be perceived by those skilled in the art without departing from the scope of the invention as defined by the following claims.

What is claimed is:

1. A wire cutting system for resecting a bone through incisions of the type utilized for arthroscopic procedures, the system comprising:
    a first alignment pin configured to be inserted through one of the incisions into a bone in a first orientation;
    a second alignment pin configured to be inserted through one of the incisions into the bone in a second orientation;
    a wire saw; and
    a guide block formed to include a first guide hole extending through the block, the first guide hole being sized to receive a drill sized to form a hole in the bone, the hole sized to receive the first alignment pin,
    wherein the first alignment pin and the second alignment pin are configured and oriented to define a resection surface of reference through which the bone is to be resected and the wire saw is configured to be inserted through at least one of the incisions and for extending at least from the first alignment pin to the second alignment pin to be simultaneously guided by the first and second alignment pins while being moved to resect the bone,
    wherein the first alignment pin has a length sufficient that the first alignment pin can extend completely through the bone with a first tip that can extend beyond the bone on a first side and a second tip that can extend beyond the bone on an opposite side of the bone, and the second alignment pin has a length sufficient that the second alignment pin can extend completely through the bone with a third tip that can extend beyond the bone on the first side and a fourth tip that can extend beyond the bone on the opposite side,
    wherein the resection surface of reference is a plane, and
    wherein the guide block is formed to include a first saw guide and a second saw guide said first and second saw guides being positioned to guide the wire saw along the resection plane of reference when the wire saw is received in the first and second saw guides.

2. The system of claim 1 wherein the first alignment pin has a length sufficient that the first alignment pin can extend completely through the bone with the first tip that can extend beyond the bone on the a first side and the second tip that can extend beyond the bone on the opposite side and into the first guide hole when the guide block is positioned on the opposite side of the bone.

3. A wire cutting system for resecting a bone through incisions of the type utilized for arthroscopic procedures, the system comprising:
a first alignment pin configured to be inserted through one of the incisions into a bone in a first orientation;
a second alignment pin configured to be inserted through one of the incisions into the bone in a second orientation;
a wire saw; and
a guide block formed to include a first guide hole extending through the block, the first guide hole being sized to receive a drill sized to form a hole in the bone, the hole sized to receive the first alignment pin,
wherein the first alignment pin and the second alignment pin are configured and oriented to define a resection surface of reference through which the bone is to be resected and the wire saw is configured to be inserted through at least one of the incisions and for extending at least from the first alignment pin to the second alignment pin to be simultaneously guided by the first and second alignment pins while being moved to resect the bone,
wherein the first alignment pin has a length sufficient that the first alignment pin can extend completely through the bone with a first tip that can extend beyond the bone on a first side and a second tip that can extend beyond the bone on an opposite side of the bone and into the first guide hole when the guide block is positioned on the opposite side of the bone, and the second alignment pin has a length sufficient that the second alignment pin can extend completely through the bone with a third tip that can extend beyond the bone on the first side and a fourth tip that can extend beyond the bone on the opposite side,
wherein the resection surface of reference is a plane,
wherein the guide block is formed to include a second guide hole extending through the guide block, the second guide hole being sized to receive a drill sized to form a hole in the bone sized to receive the second alignment pin, the second guide hole being oriented with respect to the first guide hole to define a first plane therewith,
wherein the second alignment pin has a length sufficient that the second alignment pin can extend completely through the bone with the third tip that can extend beyond the bone on the first side and the fourth tip that can extend beyond the bone on the opposite side and into the second guide hole when the guide block is positioned on the opposite side of the bone, and
wherein the guide block is formed to include a first saw guide and a second saw guide said first and second saw guides being positioned to guide the wire saw along the resection plane of reference when the wire saw is received in the first and second saw guides, the first alignment pin is received in the first guide hole and the second alignment pin is received in the second guide hole.

4. The system of claim 3 wherein the first saw guide, second saw guide, first guide hole and second guide hole define the first plane.

5. The system of claim 3 wherein the guide block is formed to include a third guide hole extending through the guide block, the third guide hole being sized to receive a drill sized to form a hole in the bone sized to receive an alignment pin, the third guide hole being oriented with respect to the first guide hole to define a second plane therewith oriented at an angle with respect to the first plane and further comprising a third alignment pin configured to be inserted through a third incision into the bone in a third orientation, the third alignment pin having a length sufficient that the third alignment pin can extend completely through the bone with a fifth tip that can extend beyond the bone on the a first side and a sixth tip that can extend beyond the bone on the opposite side.

6. A wire cutting system for resecting a bone through incisions of the type utilized for arthroscopic procedures, the system comprising:
a first alignment pin configured to be inserted through one of the incisions into a bone in a first orientation;
a second alignment pin configured to inserted through one of the incisions into the bone in a second orientation;
a wire saw; and
a saw driver configured to be guided by the first alignment pin through the bone and to drive the wire saw guided by the saw driver and the second alignment pin through the bone,
wherein the first alignment pin and the second alignment pin are configured and oriented to define a resection surface of reference through which the bone is to be resected and the wire saw is configured to be inserted through at least one of the incisions and for extending at least from the first alignment pin to the second alignment pin to be simultaneously guided by the first and second alignment pins while being moved to resect the bone,
wherein the first alignment pin has a length sufficient that the first alignment pin can extend completely through the bone with a first tip that can extend beyond the bone on a first side and a second tip that can extend beyond the bone on an opposite side and the second alignment pin has a length sufficient that the second alignment pin can extend completely through the bone with a third tip that can extend beyond the bone on the first side and a fourth tip that can extend beyond the bone on the opposite side, and
wherein the saw driver includes a shaft adapted to be driven by a rotary drill to rotate about an axis, a body coupled at a first end to the shaft to be rotated thereby about the axis, the body including a second end formed to include teeth adapted to cut through the bone and a wall extending between the first end and the second end, the wall being formed to include a driver surface for engaging the wire saw and driving the same during rotation of the body.

7. The system of claim 6 wherein the body includes a cavity formed in the second end and extending into the body toward the first end, the cavity being sized to receive the first alignment pin therein.

8. The apparatus of claim 7 wherein the wire saw forms a loop and the driver surface comprises an annular groove formed in the wall.

9. A wire cutting system for resecting a bone through incisions of the type utilized for arthroscopic procedures, the system comprising:
a first alignment pin configured to be inserted through one of the incisions into a bone in a first orientation;
a second alignment pin configured to inserted through one of the incisions into the bone in a second orientation;
a wire saw; and
a saw frame including a shaft adapted to be coupled to an oscillator, a finger coupled to the shaft at a first end for movement between a retracted position wherein a second end of the finger is adjacent the shaft and an extended position wherein the second end is displaced from the shaft and wherein the wire saw is coupled to the shaft and the finger adjacent the second end to be tensioned between the shaft and the second end when the second end is in the extended position, wherein the first alignment pin and the second alignment pin are configured and oriented to define a resection surface of reference through which the bone is to be resected and the wire saw is configured to be inserted through at least one of the incisions and for extending at least from the first alignment pin to the second alignment pin to be simultaneously guided by the first and second alignment pins while being moved to resect the bone.

10. The system of claim 9 wherein the second end is formed from a shape memory alloy.

11. The system of claim 9 wherein the first and second alignment pins and the wire saw are configured to be inserted through incisions less than six centimeters long.

12. The system of claim 11 wherein the first and second alignment pins and the wire saw are configured to be inserted through incisions less than about two centimeters long.

13. The system of claim 12 wherein the first and second alignment pins and the wire saw are configured to be inserted through incisions about one centimeter long.

14. An apparatus for resecting a bone comprising:
a wire saw;
a saw driver including a shaft adapted to be driven by a rotary drill to rotate about an axis, a body coupled at a first end to the shaft to be rotated thereby about the axis, the body including a second end formed to include teeth adapted to cut through the bone and a wall extending between the first end and the second end, the wall being formed to include a driver surface for engaging the wire saw and driving the same during rotation of the body.

15. The apparatus of claim 14 and further comprising an alignment pin sized to extend through the bone and wherein the wire saw forms a loop and is configured to engage the driver surface and be driven by the saw driver when it is rotated and driven into the bone.

16. The apparatus of claim 15 wherein the wire saw when driven is configured to be guided by the alignment pin when the pin is inserted in the bone.

17. The apparatus of claim 15 wherein the saw driver is configured to be guided by the alignment pin through the bone.

18. The apparatus of claim 17 and further comprising a second alignment pin sized to extend through the bone and wherein the wire saw forms a loop and is configured to engage the driver surface and be driven by the saw driver when it is rotated and driven into the bone and wherein the saw is configured to be guided by the saw driver and the second alignment pin through the bone.

19. The apparatus of claim 18 wherein the body includes a cavity formed in the second end and extending into the body toward the first end, the cavity being sized to receive the first alignment pin therein.

20. The apparatus of claim 14 wherein the driver surface comprises an annular groove formed in the wall.

* * * * *